United States Patent
Dodge et al.

(10) Patent No.: US 7,037,289 B2
(45) Date of Patent: May 2, 2006

(54) APPARATUS AND METHODS FOR DISPENSING AN ADHESIVE TISSUE SEALANT

(75) Inventors: Larry H. Dodge, River Falls, WI (US); Duane M. Grussing, Forest Lake, MN (US); Kristen L. Comstock, St. Paul, MN (US); David J. Velasquez, Cannon Falls, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/953,037

(22) Filed: Sep. 12, 2001

(65) Prior Publication Data
US 2003/0050597 A1    Mar. 13, 2003

(51) Int. Cl.
*A61M 37/00*    (2006.01)
(52) U.S. Cl. .......................................... 604/88; 604/191
(58) Field of Classification Search .................. 604/82, 604/86–89, 93.01, 191, 187, 181; 606/1, 606/93
See application file for complete search history.

(56) References Cited

U.S. PATENT DOCUMENTS

| | | | |
|---|---|---|---|
| 563,769 A | 7/1896 | Howard | |
| 1,642,933 A | 9/1927 | McGrath | |
| 2,631,563 A | 3/1953 | Perry et al. | |
| 2,755,968 A | 7/1956 | Fiant | |
| 2,943,338 A | 7/1960 | Lowen | |
| 3,943,628 A * | 3/1976 | Kronman et al. ............. 433/89 |
| 4,740,194 A | 4/1988 | Barabino et al. | |
| 4,887,924 A | 12/1989 | Green | |
| 4,974,748 A | 12/1990 | Rae | |
| 4,978,336 A | 12/1990 | Capozzi et al. | |
| 5,006,004 A | 4/1991 | Dirksing et al. | |
| 5,044,803 A | 9/1991 | Kurosawa et al. | |
| 5,078,527 A | 1/1992 | Bell | |
| 5,080,493 A | 1/1992 | McKown et al. | |
| 5,108,403 A | 4/1992 | Stern | |
| 5,116,315 A | 5/1992 | Capozzi et al. | |
| 5,386,928 A | 2/1995 | Blette | |
| 5,423,752 A * | 6/1995 | Haber et al. .................. 604/86 |
| 5,583,114 A | 12/1996 | Barrows et al. | |
| 5,697,903 A * | 12/1997 | Fischer ........................ 604/82 |
| 5,779,053 A | 7/1998 | Partika et al. | |
| 5,865,555 A | 2/1999 | Dawson | |
| 6,053,184 A | 4/2000 | DeVone | |
| 6,155,265 A | 12/2000 | Hammerslag | |
| 6,196,746 B1 | 3/2001 | Onischuk | |
| 6,228,051 B1 | 5/2001 | Trumbull | |

FOREIGN PATENT DOCUMENTS

| | | |
|---|---|---|
| EP | 0 933 039 A1 | 8/1999 |
| EP | 1 005 806 A1 | 6/2000 |

(Continued)

*Primary Examiner*—Nicholas D. Lucchesi
*Assistant Examiner*—Matthew F. DeSanto
(74) *Attorney, Agent, or Firm*—Kevin W. Raasch; Daniel R. Pastirik

(57) ABSTRACT

The present invention provides an improved dispenser suitable for quickly and easily setting up and dispensing multi-part tissue sealants or other multi-part compositions requiring separation of the components until just prior to application on the tissue surface. The invention may further include an applicator having a handle and a blade attached to a first end of the handle. The invention may also include a dispensing tip having a blade attached to the distal end of the dispensing tip.

10 Claims, 22 Drawing Sheets

FOREIGN PATENT DOCUMENTS

| | | |
|---|---|---|
| FR | 2098017 | 3/1972 |
| FR | 2 653 008 | 8/1989 |
| JP | 2001-97435 | 10/2001 |
| WO | WO 99/20328 | 4/1999 |

* cited by examiner

APPARATUS AND METHODS FOR DISPENSING AN ADHESIVE TISSUE SEALANT

TECHNICAL FIELD

The invention relates generally to the dispensing of adhesive tissue sealants and other liquid preparations, including those requiring mixing immediately prior to use.

BACKGROUND

A variety of techniques have been used to bond or seal living tissue. For example, different types of tissues have been mechanically bound or sealed with a number of procedures, materials and methods including sutures, staples, tapes and bandages. In some applications, these materials are made of absorbable materials that are intended to bond and/or seal tissue as it heals and then to be absorbed over a period of time.

A recent addition to the techniques that can be used is application of an absorbable adhesive sealant composition to bond and/or seal tissue. The adhesive composition is readily formed from a two component mixture that includes a first part of a cross-linking agent and a second part of a protein, preferably a serum protein such as albumin. When the two parts of the mixture are combined, the mixture is initially liquid. The combined mixture then cures in vivo on the surface of tissue to give a substantive composition that securely bonds to the tissue. Additional details can be found in commonly owned U.S. Pat. No. 5,583,114, "ADHESIVE SEALANT COMPOSITION," to Barrows et al.

The tissue sealants often have low viscosity immediately after being constituted. Although the low viscosity may be advantageous when dispensing the tissue sealant, it may cause difficulties in maintaining the tissue sealant in place on the desired tissue or other surface while the tissue sealant cures or otherwise thickens. For example, the low viscosity of the tissue sealant may result in excessive runoff when the tissue sealant is applied to angled, rounded, or vertical surfaces. The tissue sealant that runs off may pool at the lowest point in adjacent surgical tissue. Additionally, applying tissue sealant to the underside of vessels or other tissue may be difficult using traditional techniques of spraying, dripping or streaming the tissue sealant.

SUMMARY OF THE INVENTION

The present invention provides an improved dispenser suitable for quickly and easily setting up and dispensing multi-part tissue sealants or other multi-part compositions requiring separation of the components until just prior to application on the tissue surface.

The invention may include an applicator having a handle and a blade attached to a first end of the handle. The applicator may be used to catch sealant that tends to run off of the surface of tissue. The applicator may then be used to spread the sealant back onto the top and sides of the tissue in a painting or troweling fashion, which also helps to apply sealant to the underside of tissue surfaces or vessels that may normally be difficult to access. Additionally, use of the applicator allows application of sealant onto the vertical or angled sides of organs and vessels by catching the sealant as it is dripped or sprayed onto the tissue surface. Normally, much of the sealant could run off of the tissue, but the applicator may allow the user to capture and/or distribute the sealant onto the tissue in a painting or troweling fashion to achieve a uniform thickness over the desired area.

Alternatively, or in addition to the applicator described above, the invention may include a dispensing tip having a blade attached to the distal end of the dispensing tip. The blade that is attached to the dispensing tip may be flexible. Use of the dispensing tip with a blade may reduce the amount of sealant needed to coat a given area because the sealant may be more precisely applied and/or distributed.

The blades, whether provided attached to a separate applicator or attached to the dispensing tip, may allow for a back and forth painting motion that delivers a thin uniform thickness of sealant and tends not to disturb previously applied layers of sealant. Treatments and features such as coatings, embossing, micro-replicated bosses, and dams may be applied or built into the blades to create special effects. Mixing and channeling features may also be incorporated to enhance flow characteristics, thus permitting multiple sealant components, and simplifying and lowering the cost of the tip assembly. The shape of the blade may be altered to allow varying thicknesses, widths, and end features.

In one aspect, the present invention provides a kit having components useful for preparing and delivering a tissue sealant and/or adhesive having first and second components, including a first container including a septum, wherein at least a portion of the first component is contained within the first container; a second container including a septum, wherein at least a portion of the second component is contained within the second container; a sterile housing including first and second piercers located in protected positions and a portion that is sized and shaped to receive the first and second containers; and an applicator that includes a handle including a longitudinal axis, and a blade attached to a first end of the handle.

In another aspect, the present invention provides a kit having components useful for preparing and delivering a tissue sealant and/or adhesive having first and second components, including a first container including a septum, wherein at least a portion of the first component is contained with the first container; a second container including a septum, wherein at least a portion of the second component is contained within the second container; a sterile housing including first and second piercers located in protected positions and a portion that is sized and shaped to receive the first and second containers; and a dispensing tip including a longitudinal axis, wherein the dispensing tip is attachable to the housing, and further wherein a blade is attached to a distal end of the dispensing tip.

In another aspect, the present invention provides a method of preparing a multiple component tissue sealant and/or adhesive by providing a first container including a septum and a dry powder stored therein; providing a second container including a septum and a liquid second component contained within the second container; providing a housing including first and second piercers located in protected positions and a portion that is sized and shaped to receive the first and second containers; placing a solvent for the dry powder in the first container wherein the solvent solubilizes the dry powder to produce a first component; installing the first and second containers in the housing, piercing the septum of the first container with the first piercer, piercing the septum of the second container with the second piercer, wherein a user is not exposed to physical contact with the first and second piercers; and providing an applicator that includes a handle including a longitudinal axis and a blade attached to a first end of the handle.

In another aspect, the present invention provides a method of preparing a multiple component tissue sealant and/or adhesive by providing a first container including a septum and a dry powder stored therein; providing a second container including a septum and a liquid second component contained within the second container; providing a housing including first and second piercers located in protected positions and a portion that is sized and shaped to receive the first and second containers; placing a solvent for the dry powder in the first container wherein the solvent solubilizes the dry powder to produce a first component; installing the first and second containers in the housing, piercing the septum of the first container with the first piercer, piercing the septum of the second container with the second piercer, wherein a user is not exposed to physical contact with the first and second piercers; and attaching a dispensing tip to the housing, the dispensing tip including a longitudinal axis, wherein a blade is attached to a distal end of the dispensing tip.

In another aspect, the present invention provides a method of applying a multiple component tissue sealant by providing a first component; providing a second component; mixing the first component with the second component in a dispenser to provide a tissue sealant; providing an applicator that includes a handle including a longitudinal axis and a blade attached to a first end of the handle; dispensing the tissue sealant with the dispenser; and manipulating the applicator such that the blade spreads the tissue sealant.

In another aspect, the present invention provides a method of applying a multiple component tissue sealant by providing a first component; providing a second component; mixing the first component with the second component in a dispenser to provide a tissue sealant; providing a dispensing tip on the dispenser, the dispensing tip including a longitudinal axis, wherein a blade is attached to a distal end of the dispensing tip; dispensing the tissue sealant from the dispensing tip; and manipulating the dispensing tip such that the blade spreads the tissue sealant.

In another aspect, the invention features a dispenser having a container (e.g., a carpule) with at least a portion of a first component of a multi-part tissue sealant and/or adhesive (e.g., a dry powder) having a septum at one end, an open end opposite the septum, and a movable plug. The powder may be retained at the septum end of the container by the movable plug, which is preferably displaced and pushed back as a solvent used for reconstituting the powder is introduced (e.g., through the septum). At least a portion (and preferably all) of a second component of the tissue sealant (e.g. a liquid) is contained within a second container, also with a movable plug. After the first component is reconstituted, a housing (preferably a manifold) having piercers is used to pierce both septums and allow the contents to be dispensed. Preferably, the piercers are placed in a protected position so as not to expose a user to contact with the piercers. A body supports the containers. Pistons are provided to advance the movable plugs.

Preferred implementations of this aspect of the invention may include one or more of the following features.

The first component may be a dry powder of a water-compatible or water-soluble cross-linking agent.

The aqueous solution for dissolving the powder may be introduced through the first septum (e.g., either via the piercer or via an injection through the septum by a syringe).

The movable plug may be positioned in a position in which the space between the plug and the septum is substantially the minimum necessary to contain the dry powder, thereby reducing the amount of air in that space and consequently the amount of pressure rise associated with injecting liquid through the septum. The movable plug can move away from the septum as liquid is injected to reduce any pressure rise.

The second component stored in the second carpule may be a solution.

The second component may be a protein dissolved in an aqueous buffer and capable of reacting with the solution of the first component to provide the adhesive tissue sealant.

The body may include a retainer for protecting and/or holding the containers.

In another aspect, the invention features an improved manifold for a two-part dispenser. Two containers (e.g., carpules), each having a septum at one end, an open end opposite the septum, and a movable plug, are supported in a dual syringe body, which has pistons configured to enter the open ends of the containers to advance the movable plugs. A manifold has cavities that receive the septum ends of the containers, and a disk supporting a piercer (e.g., hollow needle) is mounted in the base of each cavity so that the septum of a container is pierced when it is installed in a cavity. Each disk is supported a distance above the base of a cavity to form a plenum defined by the disk and adjacent walls of the base of the cavity. Liquid exiting a container travels through the lumen of the piercer, then into the adjacent plenum, and then out of the plenum along a conduit extending to the nozzle. This arrangement of disks each supporting a piercer and forming a plenum provides an effective, relatively low-cost way of constructing a manifold for connecting carpule piercers to a common nozzle.

Preferred implementations of this aspect of the invention may include one or more of the following features.

Each disk may be sealed to the surrounding wall of the cavity (e.g., by an elastomeric sealing member on the disk) so that the adjacent plenum is defined by the disk and the base of the cavity.

The conduit and piercer lumen may each communicate with the plenum at laterally spaced apart locations so that flow from the piercer lumen to the conduit changes direction from a generally longitudinal flow path through the piercer lumen, to a generally lateral direction in the plenum, and then to a generally longitudinal flow path in the conduit.

The disk may be supported from the base of the cavity by standoffs.

The first container may contain a quantity of the first component in the form of a dry powder so that the first component must be dissolved prior to use by introduction of an aqueous solvent.

The second container may contain a quantity of protein in an aqueous buffer that is capable of reacting with a dissolved first component to provide an adhesive tissue sealant.

In another aspect, the invention features a method for dispensing a component stored in a dispenser in dry powder form and reconstituted by introduction of a solvent. A carpule is provided with a septum at one end, an open end opposite the septum end, and a movable plug disposed there between. The dry powder is stored between the septum and the movable plug. Solvent is introduced into the interior of the container by piercing the septum with a syringe and injecting the solvent into the carpule. The carpule is installed in a syringe body and manifold, the latter providing a flow path from the piercer to an outlet nozzle.

Preferred implementations of this aspect of the present invention may include one or more of the following features.

Installing the carpule in the syringe body and manifold may occur before or after the solvent is injected through the septum.

The first movable plug may be positioned in a position in which the space between the plug and the septum is substantially the minimum necessary to contain the dry powder, thereby reducing the amount of air in that space and reducing the pressure increase within the carpule when the solvent is introduced by piercing the first septum. The movable plug can move away from the septum as liquid is injected to reduce any pressure rise.

The dispenser may include a second carpule comprising a second septum at one end, an open end opposite the second septum, and a second movable plug disposed therein, the second carpule containing a second component, and the syringe body and manifold may be sized and configured to accept the first and second carpule.

The second component may be a protein in an aqueous buffer and capable of reacting with the first component to provide an adhesive tissue sealant.

The dry powder of the first component may be a water-compatible or water-soluble cross-linking agent capable of reacting with the second component to provide the adhesive tissue sealant.

In another aspect, the present invention includes a kit having components useful for preparing and delivering a tissue sealant and/or adhesive having first and second components. The kit includes a first container having a septum, at least a portion of the first component stored therein, and outer portions. The kit includes a second container having at least a portion of the second component therein, a septum, and outer portions. At least one vial with a solvent for at least one of the first and second components is also present in the kit. The kit further includes a syringe and needle; and a sterile housing having first and second piercers located in protected positions and a portion that is sized and shaped to receive the first and second containers.

In another aspect, the present invention includes a method of preparing a multiple component tissue sealant and/or adhesive just prior to use comprising the steps of providing a first container having a septum and a dry powder stored therein; providing a second container having a septum and a liquid therein; providing a vial with a solvent for the dry powder therein; providing a syringe and needle; providing a housing having first and second piercers located in protected positions and a portion that is sized and shaped to receive the first and second containers; withdrawing the solvent from the vial with the syringe and needle; placing the solvent in the first container; and installing the first and second containers in the housing and piercing the septums of the first and second containers with the first and second piercers without exposing a user to physical contact with the piercers.

Other features and advantages of the invention will be apparent from the following description and drawings, and from the claims.

BRIEF DESCRIPTION OF THE DRAWINGS

FIGS. 18 through 26 illustrate steps in the use of a kit according to one aspect of the present invention wherein:
FIG. 18 illustrates a syringe and needle being loaded with a solvent;
FIG. 19 illustrates the loaded syringe (after being loaded with solvent in the operation depicted in FIG. 18) being used to fill a first container with the solvent to dissolve a first component of a tissue adhesive and/or sealant within the first container;
FIG. 20 illustrates optional additional manual mixing of the first component of a tissue adhesive and/or sealant within the first container;
FIG. 21 illustrates a container being loaded into the housing of a tissue adhesive and/or sealant dispenser;
FIG. 22 shows a dual piston being received in open ends of first and second containers of the dispenser;
FIG. 23 illustrates an optional step of expressing air from the dispenser preassembly;
FIG. 24 illustrates an optional step of cleaning the surface of the housing of the dispenser;
FIG. 25 shows a dispensing tip being attached to the dispenser;
and
FIG. 26 illustrates the assembled dispenser being used to dispense a tissue adhesive and/or sealant composition.

DETAILED DESCRIPTION

Figure 1:
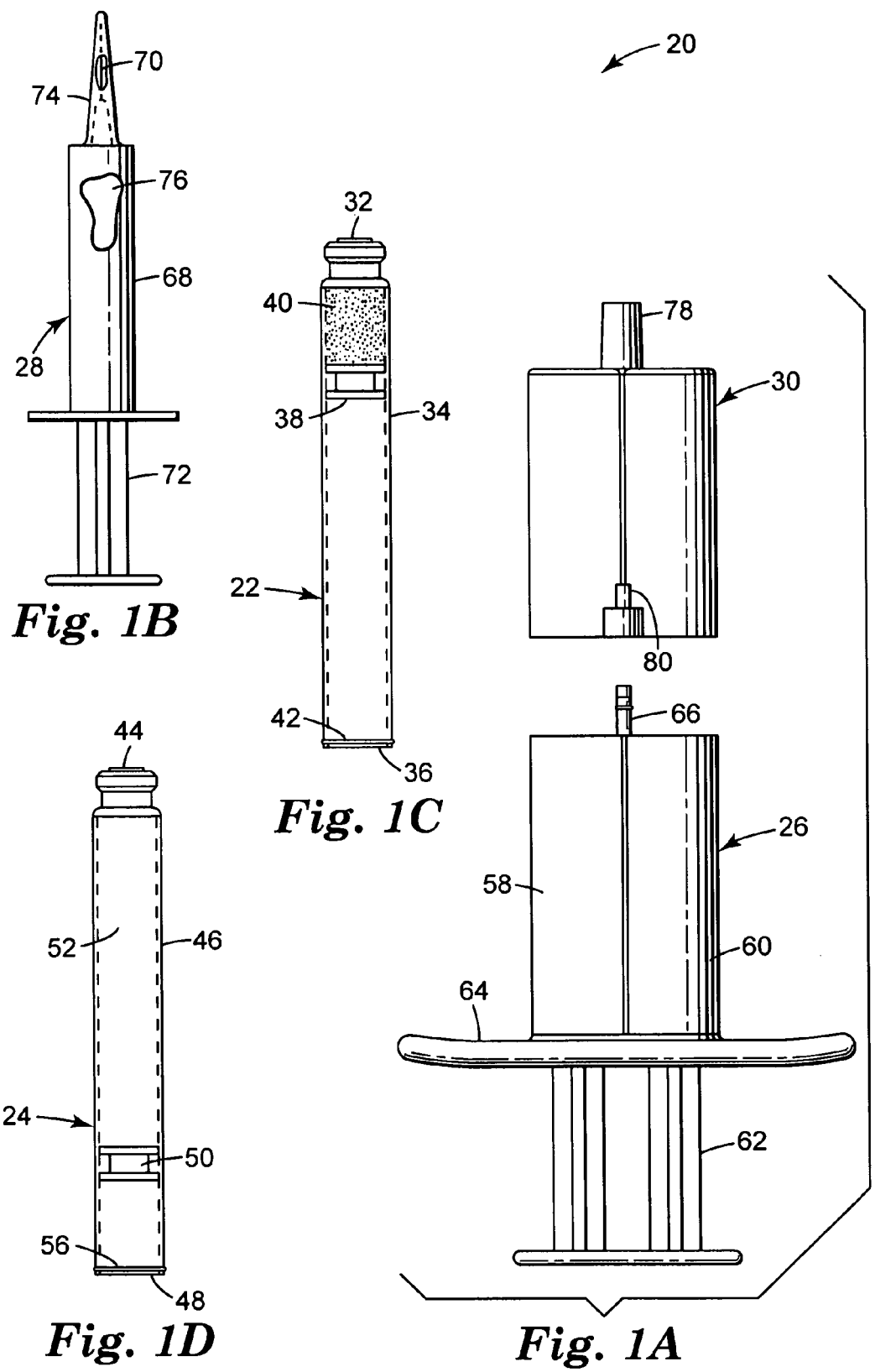
FIGS. 1A–1D are side views of elements of a preferred embodiment of the invention.

The present invention provides additional features over those discussed in U.S. patent application Ser. No. 09/524, 141, filed Mar. 10, 2000 and U.S. patent application Ser. No. 08/956,308 filed Oct. 22, 1997.

Those kits are described first below, with kits including the applicators and bladed dispensing tips of the present invention following.

Referring now to FIGS. 1A–1D, side views of an example of the elements of a dispenser kit 20 according to the present invention are illustrated. The dispenser kit 20 includes a first carpule 22, a second carpule 24, a dual syringe body 26 adapted to receive and support the first and second carpules, a syringe 28, and a manifold (nozzle body) 30. First carpule 22 has a first septum 32 at one end of first carpule body 34, the other end of the first carpule body being an open end 36. There is a first movable plug 38 disposed within the first carpule 22 so that a quantity of a first component 40 is contained between the first septum 32 and the first movable plug. In preferred embodiments, first component 40 is a quantity of dry powder of a water-compatible or water-soluble multi-functional cross-linking agent. Conveniently, the first carpule body 34 has a ridge 42 near open end 36 to facilitate the retaining of the first carpule within dual syringe body 26.

First movable plug 38 is positioned so that the space between the plug and the septum is substantially the minimum necessary to contain the dry powder, thereby reducing the amount of air in the space between the plug and septum. Reducing the amount of air entrapped with the powder has the benefit that when solvent is injected into the carpule to dissolve the powder there is less rise in pressure within the carpule, as the plug is able to move away from the septum to reduce any pressure rise. Elevated pressure is undesirable in that it could lead to difficulty when the solvent is injected into the carpule and when the carpule is later pierced on insertion in the manifold 30. An elevated pressure could result, once piercing occurs, in immediate flow of the first component into the manifold and nozzle.

Second carpule 24 has a second septum 44 at one end of second carpule body 46, the other end of the second carpule body being an open end 48. There is a second movable plug 50 disposed within the second carpule 24 so that a quantity of a second component 52 is contained between the second septum 44 and the second movable plug. In preferred embodiments, second component 52 is a quantity of protein in an aqueous buffer. Conveniently, the second carpule body 46 has a ridge 56 near open end 48 to facilitate the retaining of the second carpule within dual syringe 26.

Preferably, first and second movable plugs 38 and 50 include a lubricant. In a preferred embodiment, the lubricant includes a coating of silicone. The lubricant facilitates movement of the plugs relative to the rest of the containers 22 and 24.

Also preferably, the first and second septums 32 and 44 are fixed to the containers (e.g. carpules) 22 and 24 by aluminum caps. The elongate cylindrical portion of the containers 22 and 24 may be glass in one preferred embodiment. The glass allows the user to see the contents of the containers 22 and 24.

Dual syringe body 26 includes a base 57 having two cylinders 58 and 60 adapted to receive and support the first and second carpules 22 and 24. A dual piston 62 is provided, adapted to enter the open ends 36 and 48 of the carpules 22 and 24 so as to contact and advance the first and second movable plugs 38 and 50. A flange 64 is provided to allow the practitioner to grip the dual syringe body 26 during injection in the conventional manner for syringes. A pair of latches 66 (only one being visible in this view) are provided to attach dual syringe body 26 to manifold 30.

Syringe 28 is conveniently of conventional type, having a body 68, a nozzle or needle 70 at one end, and a piston 72 at the other end. A protective cap 74 is provided to preserve the needle 70 in a sterile condition until the kit is to be used. The needle 70 is adapted to pierce the first septum 32 for injecting the aqueous solvent 76 contained within syringe 28 into the first carpule 22. In a preferred embodiment, solvent 76 is pyrogen free sterile water (e.g. USP water for injection) for dissolving the dry powder of a water-compatible or watersoluble multi-functional cross-linking agent.

Manifold 30 is adapted to fit over and pierce the first and second septums 32 and 44 after the first component 40 has been mixed with the solvent 76. Manifold 30 has a dual nozzle 78, which in the preferred embodiment keeps the first and second components 40 and 52 completely separate until just after the moment of dispensing. A pair of receptacles 80 (only one being visible in this view) are provided to attach dual syringe body 26 to manifold 30 by receiving latches 66. Optionally, the kit 20 may include a static mixer and/or dispensing tip that is adapted to be fitted onto nozzle 78.

Figure 2:
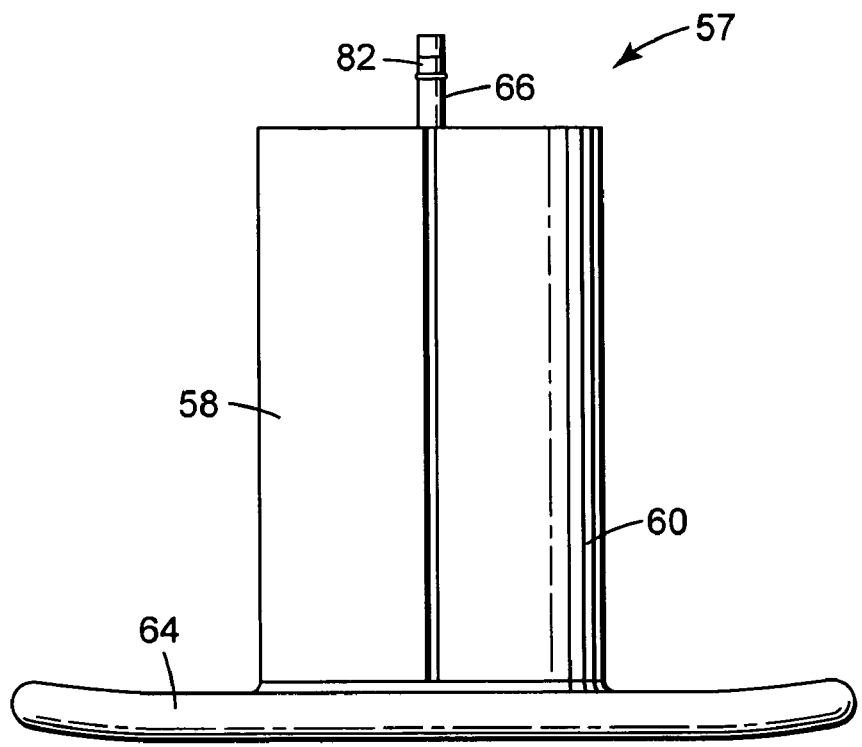
FIG. 2 is a side view of the base of the dual syringe body.
Figure 3:
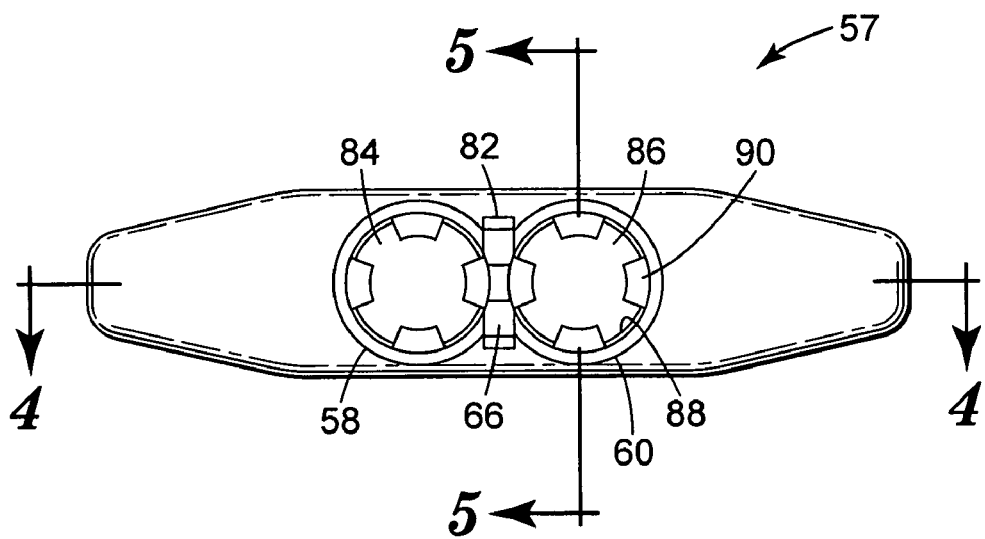
FIG. 3 is a bottom view of the base of FIG. 2.

Referring now to FIG. 2, a side view of the base 57 of the dual syringe body 26 is illustrated in isolation. It will be noted that the latches 66 each have a projection 82 which allows them to interact with the receptacles 80 as discussed above. Referring now to FIG. 3, a bottom view of the base 57 of FIG. 2 is illustrated. In this view it can be seen that cylinders 58 and 60 have internal through bores 84 and 86 respectively which are sized to receive first and second carpules 22 and 24 (shown in FIGS. 1A–1D). It can also be seen that projecting inwards from the walls of each of the cylinders 58 and 60 are four tapered ledges 88 which interact with ridges 42 and 56 of first and second carpules 22 and 24 respectively to retain the carpules within the bores 84 and 86.

Figure 4:
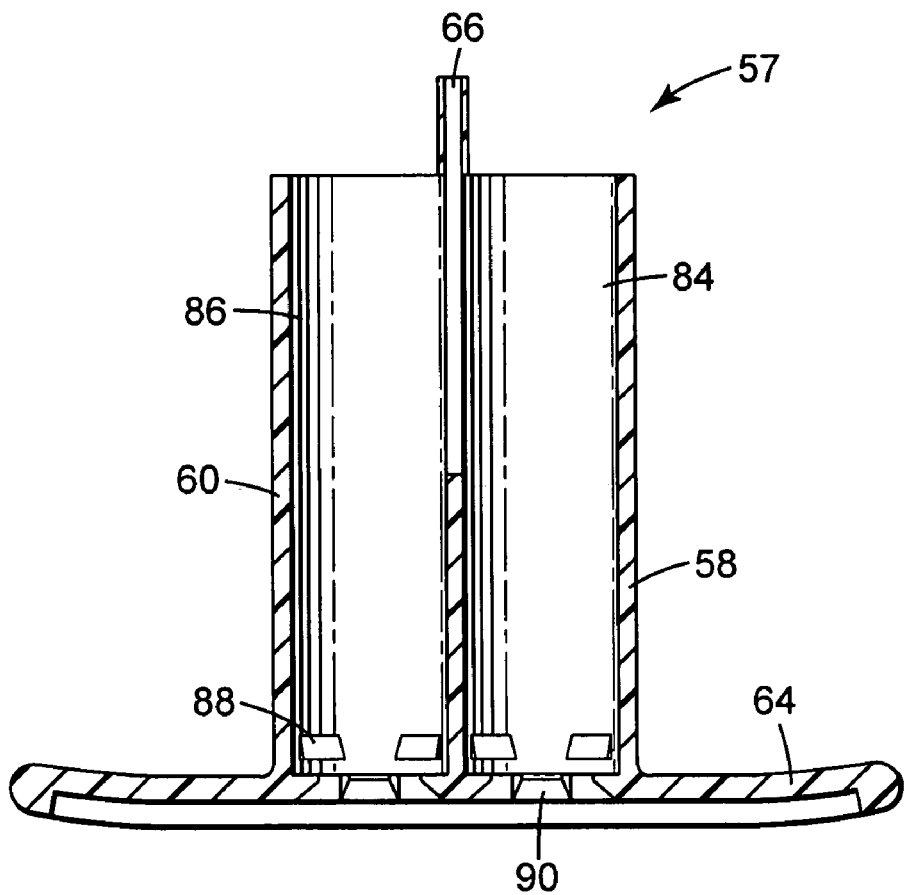
FIG. 4 is a cross-sectional view taken along section lines 4—4 in FIG. 3.
Figure 5:
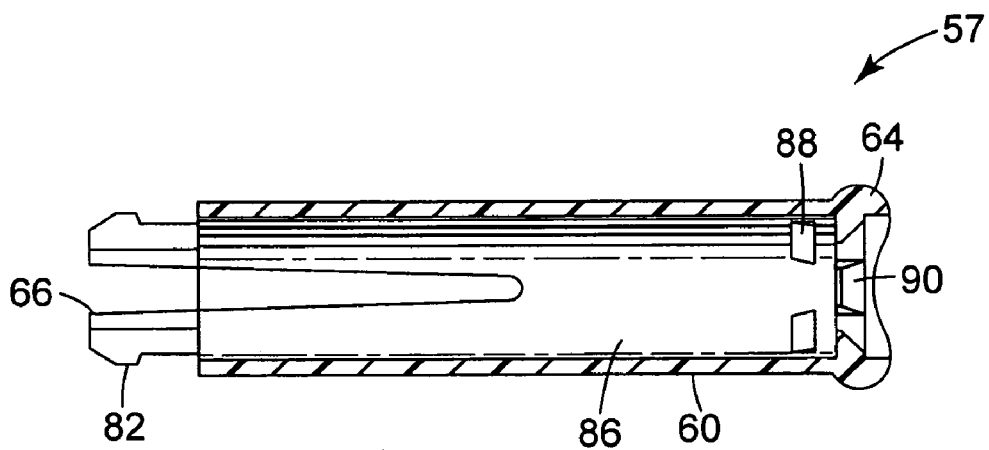
FIG. 5 is a cross-sectional view taken along section lines 5—5 in FIG. 3.

Referring now to FIG. 4, a cross-sectional view of base 57 taken along section lines 4—4 in FIG. 3 is illustrated. In this view it can be seen that projecting inwards from the walls of each of the cylinders 58 and 60 are four tapered retainers 90 which interact with and retain dual piston 62 within the bores 84 and 86. This will be discussed in more particularity below. In FIG. 5, a cross-section view of base 57 taken along section lines 5—5 in FIG. 3 is illustrated so that the features of the base can be more readily seen.

Figure 6:
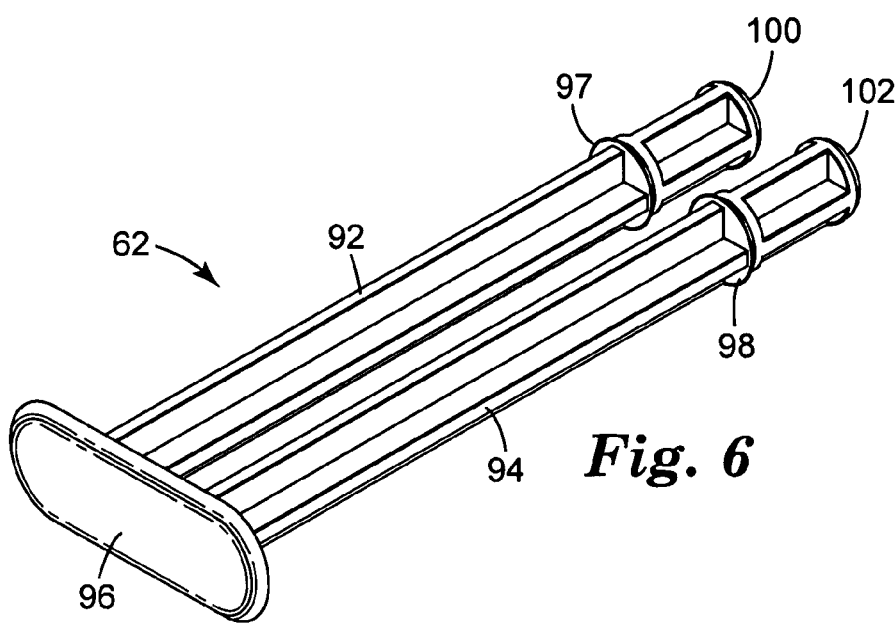
FIG. 6 is a perspective view of the dual piston.
Figure 7:
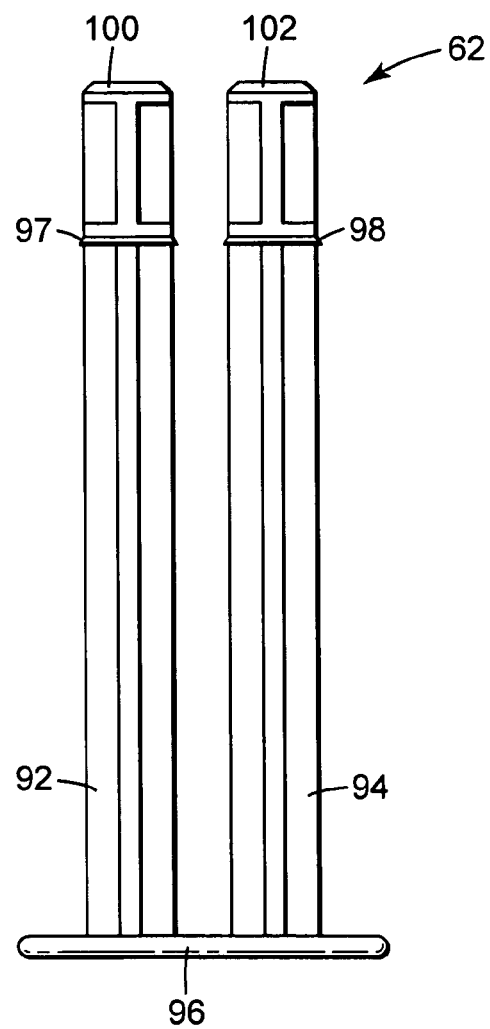
FIG. 7 is a side view of the dual piston of FIG. 6.

Referring now to FIGS. 6 and 7, views of dual piston 62 are illustrated.

A pair of push rods 92 and 94 extend from a thumb plate 96. Each of the push rods 92 and 94 has a circumferential ridge 97 and 98 adapted to interact with the tapered retainers 90 discussed in connection with FIGS. 4 and 5 to retain dual piston 62 within bores 84 and 86. The free ends 100 and 102 are intended to contact movable plugs 38 and 50 (seen in FIGS. 1A–1D) to advance them and pressurize the fluid in carpules 22 and 24 when pressure is exerted by the hand of the practitioner on the thumb plate 96.

Figure 8:
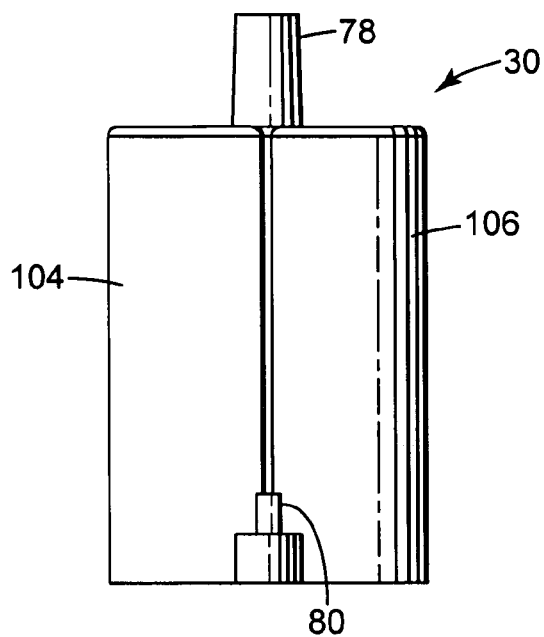
FIG. 8 is a side view of the manifold.

Referring now to FIG. 8, a side view of the manifold 30 is illustrated in isolation. The manifold 30 includes barrels 104 and 106 which are sized and shaped to enclose the ends of the of carpules 22 and 24 having septums 32 and 44 when the carpules have been inserted into the base 57 and the manifold has been attached to the base by interlocking latches 66 with receptacles 80.

Figure 9:
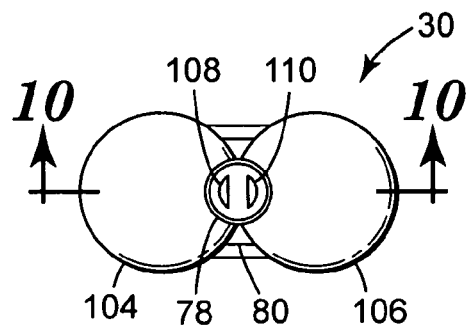
FIG. 9 is a bottom view of the manifold of FIG. 9.

Referring now to FIG. 9, a bottom view of manifold 30 of FIG. 8 is illustrated. In this view it can be seen that nozzle 78 includes openings 108 and 110 to allow the components in carpules 22 and 24 to be dispensed as separate solutions. A further nozzle element (not shown) could be installed over nozzle 78 to contain and promote mixing of the two streams of liquid emerging from openings 108 and 110.

Figure 10:
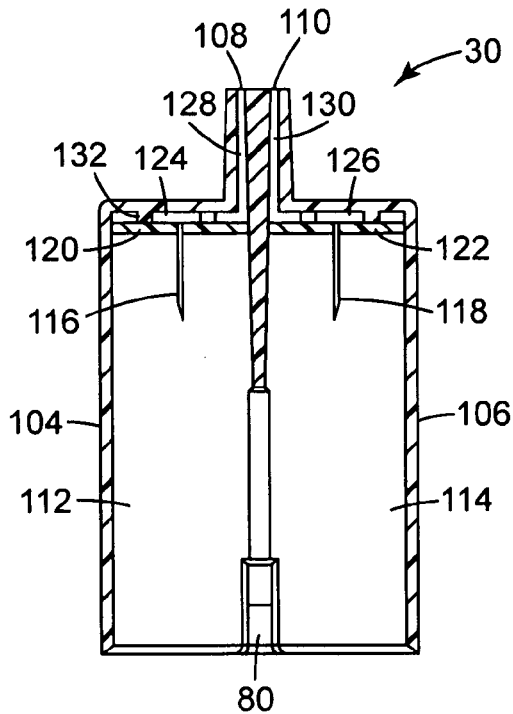
FIG. 10 is a cross-sectional view taken along section lines 10—10 in FIG. 9.

Referring now to FIG. 10, a cross-sectional view taken along section lines 10—10 in FIG. 9 is illustrated. It can now be seen that barrels 104 and 106 have cylindrical, hollow interiors (or cavities) 112 and 114 respectively to receive the carpules 22 and 24. A pair of piercers 116 and 118 are provided to pierce the septums 32 and 44 when the manifold 30 is mounted on the base 57. The piercers are conveniently mounted on mounting disks 120 and 122, the edges of which form a seal with the walls of cylinders 104 and 106. This may be conveniently accomplished by solvent bonding, by ultrasonic welding, or by having an elastomeric member (e.g., an o-ring within a groove) along the edge of the mounting disks 120 and 122 which contact the walls 104 and 106 and hold the mounting disks 120 and 122 in place by friction fit. Access is available for the contents of carpules 22 and 24 through the hollow central bore of each of the piercers into plenums 124 and 126 and on into passageways (or conduits) 128 and 130 to openings 108 and 110. Several standoffs 132 are conveniently molded into the base of cavities 112 and 114 to position the mounting disks 120 and 122 in the right location to provide for plenums 124 and 126.

The dispenser kit is easily sterilized. In one embodiment, the carpules can be sterile filled or e-beam sterilized, and the assembled kit undergoes a terminal sterilization (e.g., with ethylene oxide gas or gamma or e-beam irradiation).

Figure 11:
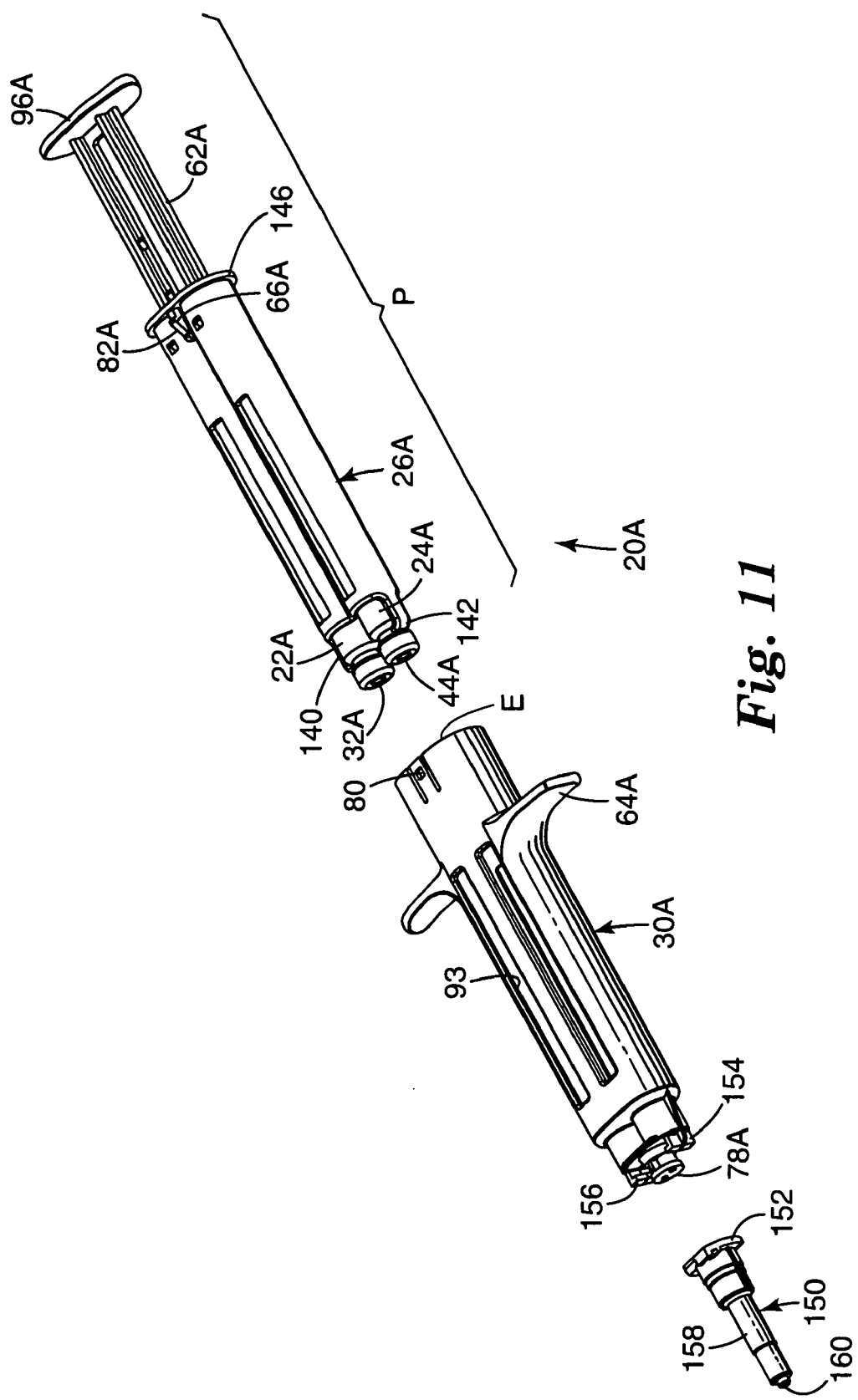
FIG. 11 is a perspective exploded view of elements of an alternate embodiment of the invention.

Referring now to FIG. 11, a perspective view of an alternate embodiment of several of the elements of a dispenser 20A according to the present invention is illustrated. The dispenser 20A includes first container 22A and second container 24A with movable plugs 38A and 50A; housing 30A and a dual syringe body 26A. The dual syringe body 26A is sized and shaped to receive and support the containers 22A and 24A.

The housing 30A includes a manifold. Latches 66A (only one being visible in FIG. 11) are provided to attach dual syringe body 26A to housing 30A. The latches 66A are preferably located at the proximal end of the dual syringe body 26A. The latches 66A preferably include projections 82A that are still sized and shaped to be received in receptacles 80A in the housing 30A so as to snap-connect the housing 30A to the dual syringe body 26A.

Optionally, the containers 22A and 24A (preferably carpules), dual syringe body 26A and piston 62A may be brought together into a preassembly P as shown in FIG. 11. The preassembly P makes the task of insertion of the containers 22A and 24A into the housing 30A more convenient as a user can accomplish this by simply sliding the preassembly into the housing.

Alternatively, the latches 66A, projections and receptacles 80A may be sized and shaped so that preassembly P may be easily, manually removed from the housing 30A. The latches 66A, projections and receptacles 80A are designed so that the preassembly P may be manually releasable. In some surgical procedures, it may be desirable to replace spent carpules with new carpules. With the embodiment described with releasable latches, it can be seen that at least portions of the dispenser 20A may be reused. This can be especially suitable in surgical procedures that require multiple sets of carpules to deliver the tissue adhesive or sealant. Preferably, the dispenser according to the present invention is only reusable on the same patient. After the surgical procedure on the patient, the dispenser is discarded.

Finger flange 64A is provided on the housing 30A to allow the practitioner to grip the dispenser in the conventional manner. Finger springs 140 and 142 engage the shoulders of the carpules 22A and 24A to retain first and second carpules 22A and 24A within the dual syringe body 26A. A limiting shoulder 146 interengages with the proximal end E to limit the extent to which the syringe body 26A may be inserted into the housing 30A. The element that includes limiting shoulder 146 may have a hole that is sized and shaped to engage legs 92A and 94A of dual piston 62A to retain the association of the dual piston 62A with the inner portions of the carpules 22A and 24A. As a result, the tapered retainers 90 of the embodiment shown in FIG. 3 are not needed in this embodiment.

The preassembly P is readily manufacturable as the construction of the finger springs 142 and 144 is less sensitive to tolerances than the design shown in FIGS. 1–10.

The dispenser 20A may optionally include a separate dispensing tip 150 that is sized and shaped to be fitted onto nozzle 78A. The dispensing tip 150 preferably includes a base flange 152 that is adapted to engage complementary grips 154 and 156 adjacent the nozzle 78A. In a preferred embodiment, the dispensing tip 150 has a static mixing element within its barrel 158, although this is not shown in FIG. 12. Preferably, the dispensing tip 150 includes a fluidic element 160 at the tip to provide a final mixing of the two liquid components just before dispensing. Preferably, the orifice of the dispensing tip is approximately circular and between about 0.005 inches to 0.010 inches (0.012 to 0.025 mm) in diameter and about 0.003 inches (about 0.0762 mm) in length. A length to diameter of the orifice of no more than 1:2 is preferred.

Figure 12:
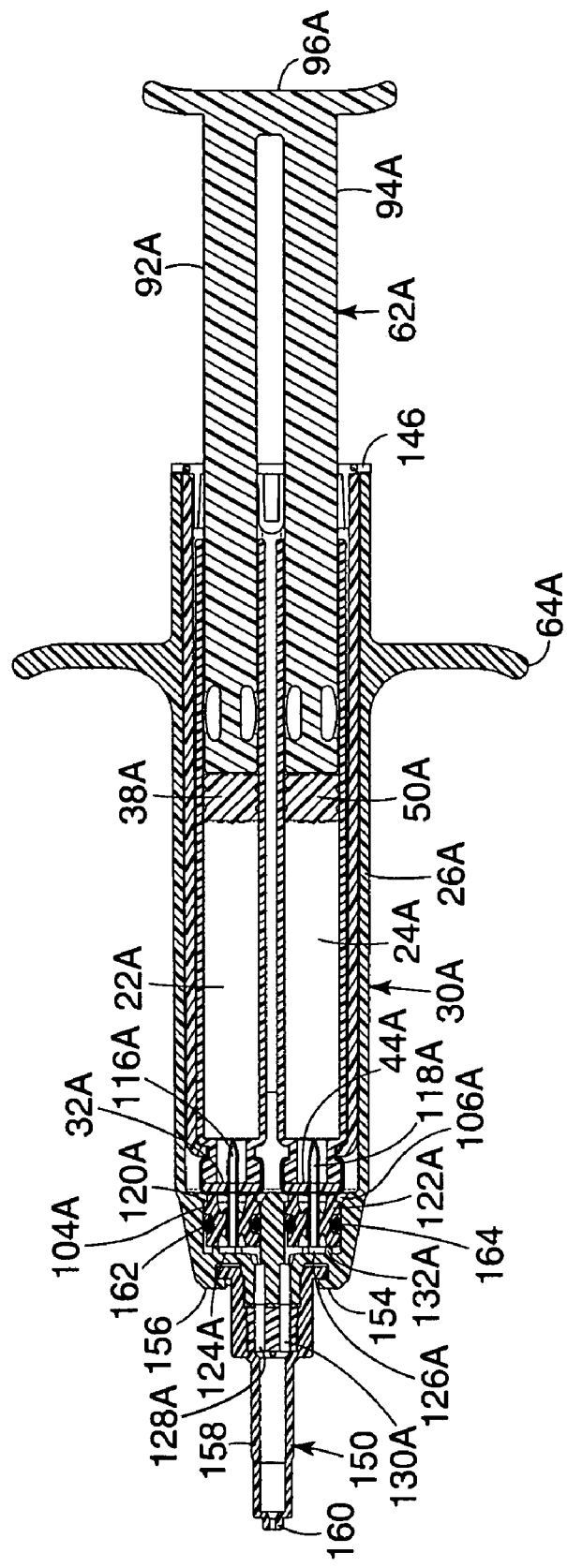
FIG. 12 is a cross-section front view of the assembled alternate embodiment of FIG. 11.

Referring now to FIG. 12, a cross-section front view of the assembled embodiment of FIG. 11 is illustrated. The details of the manifold are best seen in this view. The manifold includes piercers 116A and 118A that are situated in protected positions. By "protected positions" it is meant that a user could not readily engage the sharp surfaces of the piercers 116A and 118A. In preferred embodiments, such contact is very difficult and the likelihood of it happening is substantially reduced. Preferably, the first and second septums 32A and 44A do not contact the piercers 116A and 118A until the containers 22A and 24A are substantially inside housing 30A.

Referring to FIG. 11, if the housing 30A is opaque, the housing 30A may optionally include viewing windows or slots. The viewing windows 93 may be especially desirable if the housing 30A is constructed from a material that is opaque or if the housing is otherwise difficult to see through. The windows 93 allow the user to view the remaining portions of the tissue adhesive and/or sealant in the containers 22A and 24A. The windows 93 are preferably thin and elongate so as to substantially reduce that chance that the user will come into contact with the piercers 116A and 118A.

The piercers 116A and 118A are mounted on mounting disks 120A and 122A, the edges of each of which form a seal with the walls of cylinders 104A and 106A by means of O-rings 162 and 164. Mounting disks 120A and 122A are situated against standoffs 132A to create plenums 124A and 126A. The first and second components of the tissue sealant or adhesive may flow through passageways or conduits 128A and 130A. Once the components of the tissue sealant or adhesive exit the passageways 128A and 130A, they can then begin mixing in the dispensing tip 150. The dispensing tip 150 may be made in accordance with, e.g., the teachings of *Atomization and Sprays,* by Arthur H. Lefebvre (published by Hemisphere Publishing Corporation, U.S.A. 1989) (see, e.g., pages 112–121). Preferably, a static mixer within dispensing tip 150 is constructed to afford mixing of the first and second components of the tissue sealant or adhesive. For example, the static mixer may include a static mixer similar to the static mixers taught in U.S. Pat. Nos. 5,080,493 and 5,386,928.

Flange 64A is provided to allow the practitioner to grip the housing 30A during injection in the conventional manner for syringes. The finger flange 64A is sized and shaped to afford convenient manual grasping.

Figure 13:
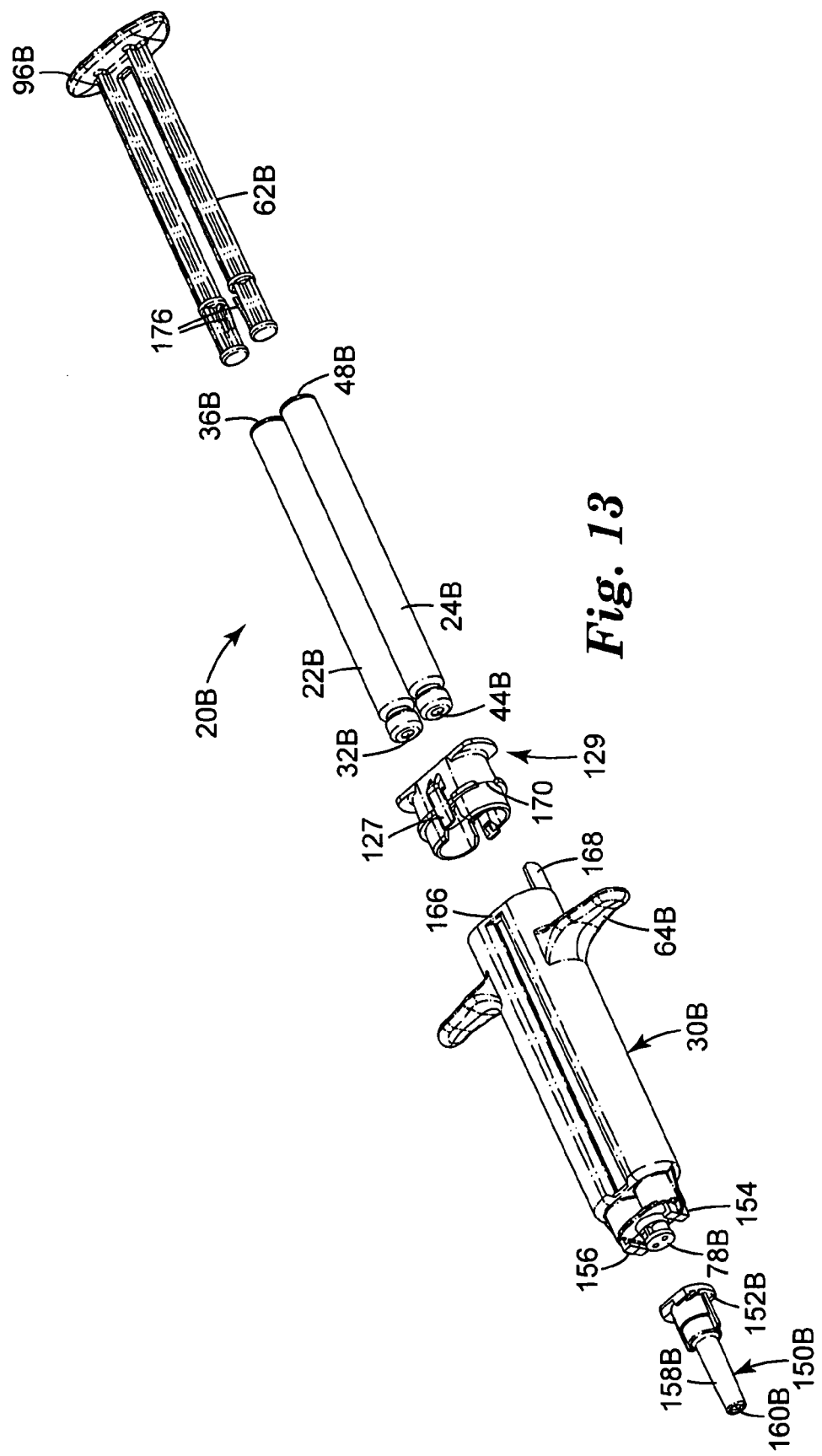
FIG. 13 is a perspective exploded view of elements of an additional alternate embodiment of the invention.
Figure 14:
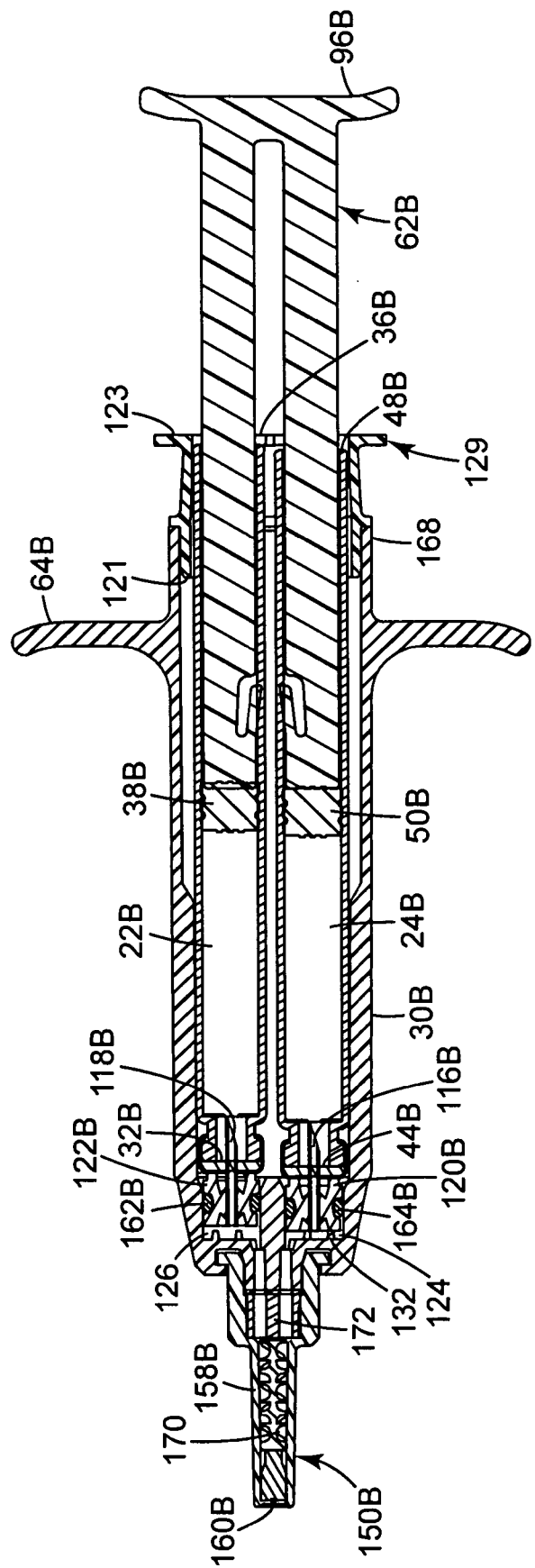
FIG. 14 is a cross-section front view of the assembled alternate embodiment of FIG. 13.

Referring now to FIGS. 13 and 14, a perspective exploded view and an assembled view of an additional alternate embodiment are illustrated. The dispenser 20B includes a housing 30B with a manifold, containers 22B and 24B, and dispensing tip 150B. The dispenser 20B is particularly suitable for simultaneously dispensing first and second components of a tissue sealant, such as, for example, the tissue sealant and/or adhesive disclosed in U.S. Pat. No. 5,583,114 to Barrows et al. Preferably, at least the first component is initially stored and/or shipped in the dispenser as dry powder. For example, the first component may initially include 130 mg Poly (ethylene glycol) di-succinimidyl succinate (PEGSS2) in powder form that is designed to be dissolved just prior to use by introduction of a solvent (e.g. about 1 ml of sterile water). Alternatively, for medical procedures that require additional amounts of tissue sealant, the first component may include 260 mg of PEGSS2 in powder form that is designed to be dissolved just prior to use by about 2 ml of sterile water.

The dispenser 20B includes a first container 22B having a first septum 32B at one end, an open end 36B opposite the first septum, and a first movable plug 38B disposed therein. The first container 22B initially contains a quantity of the first component in the form of a dry powder stored between the first septum 32B and the first movable plug 38B. The first component is preferably stored and/or shipped in a dry powder/separate solvent solution until just prior to use of the dispenser 20B to deliver or apply a tissue sealant and/or adhesive to a patient. Just prior to use of the dispenser 20B to deliver or apply a tissue sealant and/or adhesive to a patient, the dry powder may be dissolved in a solvent.

FIG. 14 illustrates the container 22B after the solvent has been added and air has been expunged.

The dispenser 20B includes a second container 24B comprising a second septum 44B at one end, an open end 48B opposite the second septum 44B, and a second movable plug 50B disposed therein. The second container 24B contains a quantity of the second component, preferably in liquid form (e.g. 1 mL Human Serum Albumin solution). Preferably, the second component is stored and shipped in this liquid form.

The dispenser 20B includes housing 30B having internal surfaces with first and second piercers 116B and 118B that are preferably sharp to pierce the first and second septums of the first and second containers 22B and 24B. The first and second piercers 116B and 118B are situated in protected positions so that the first and second septums may be pierced without exposing a user to contact with the first or second piercers 116B and 118B. The housing 30B affords passage of the first and second components via first and second flow paths to a nozzle 78B from which the first and second components are dispensed to combine to form the adhesive tissue sealant.

Pistons are sized and configured to be received in the open ends 36B and 48B of the first and second containers 22B and 24B to advance the first and second movable plugs 38B and 50B. Preferably, the pistons are provided by dual piston 62B.

A manually removable dual body in the form of retainer 129 is sized and shaped to receive the containers 22B and 24B. The retainer 129 protects and supports the containers 22B and 24B. The retainer 129 is particularly suitable when the containers 22B and 24B are constructed from glass that may be broken.

The retainer 129 may engage the proximal end of the housing 30B. Preferably the retainer 129 includes attachment means for releasably engaging the housing 30B. In a preferred embodiment, the attachment means are manually releasable and may reattach the retainer 129 to the housing 30B. The retainer 129 may, for example, be held onto the housing 30B by a press fit, or conveniently have an extending arm 127 which latches over a lip 166 near the proximal end of the housing 30B.

As best seen in FIG. 14, the retainer 129 preferably includes a distal end 121 and a proximal end 123 having an opening. The containers 22B and 24B are received in the opening of the retainer 129. The containers 22B and 24B can be easily slid through the retainer 129 so that the septums 32B and 44B may be pierced by piercers 116B and 118B. Also preferably, the retainer 129 is sized and shaped so that the open ends 36B and 48B of the first and second containers 22B and 24B do not project substantially beyond the opening of the retainer.

It may sometimes be desirable to reuse the same housing 30B during a surgical procedure on a single patient. This may be accomplished by loading new containers 22B and 24B in the housing 30B and optionally changing the dispensing tip 150B. In such a procedure, it is desirable to replace each container 22B and 24B with a container of the same substance so there will not be inadvertent premature reactions of components within the piercers 116B and 118B or plenums 124B and 126B. One way of helping insure that this occurs is to provide an indexing means (e.g. color code) the carpules 22B and 24B, conveniently by color anodizing the metal caps that retain the septums. These then can be matched up with an indexing means such as a color code on the retainer 129 and/or the housing 30B. When this is done, it is desirable to provide a specific orientation for the retainer 129 on the housing 30B. One way in which the can be conveniently accomplished is to place an optional indexing projection 168 on the housing 30B and a matching keyway 170 on the retainer 129. Alternatively, the replacement containers 22B and 24B and new body 129 may be packaged separately to provide a replacement subassembly.

Referring again to FIG. 14, a cross-section front view of the assembled alternate embodiment of FIG. 13 is illustrated. Optional static mixer 170 and an optional seal 172 are included within the dispensing tip 150B. The seal 172, when present, serves to keep the components of the tissue adhesive and/or sealant separated until the static mixing zone.

The portion of the tip 150B that includes the opening 160B is conveniently fabricated by injection molding of a polymer, with polycarbonate resin considered suitable. For example, the USP Class VI grade polycarbonate commercially available as RX2530-118 from Bayer may be used. The seal element 172 may be molded from a medical grade silicone rubber. The remaining portions of the dispensing tip 150B may be molded from medical grade polypropylene.

Figure 15:
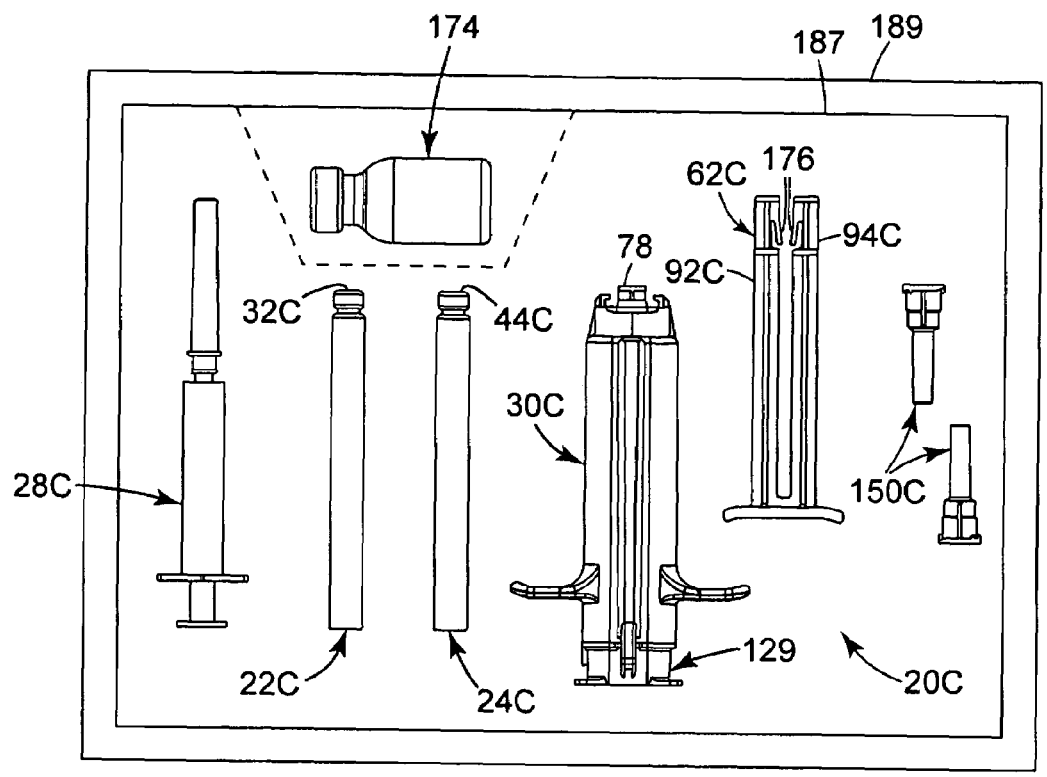
FIG. 15 is a version of a kit including the elements illustrated in FIG. 13.

FIG. 15 illustrates one example of a kit 20C according to the present invention. The kit includes elements useful for preparing and delivering a two component tissue sealant and/or adhesive just prior to use, such as the tissue adhesive/sealant described above with reference to FIGS. 13 and 14.

The kit includes first container 22C having a septum 32C and at least a portion of a first component of the tissue sealant and/or adhesive (e.g. a dry powder) stored therein, and outer portions that have preferably been sterilized, a second container 24C having at least a portion of the second component (e.g. in the form of a liquid) stored therein and a septum 44C, and outer portions that have preferably been sterilized. When the second component of the tissue adhesive and/or sealant is provided in liquid form, the kit may be free of any solution for reconstituting the second component within the second container 24C.

The kit preferably includes a vial 174 (with inner and outer portions preferably sterile) with a solvent for the dry powder therein. The kit also includes syringe and needle 28C (preferably sterile). The kit also includes dispenser capable of dispensing the tissue sealant and/or adhesive. As best seen in FIG. 14, the dispenser has first and second piercers 116B and 118B located in protected positions and a portion that is sized and shaped to receive the first and second containers.

The components of the kit 20C are packaged within a first package 187. Preferably the inside and outside portions of the elements of the kit 20C are provide in a sterile condition. More preferably, the first package 187 is packaged within a second package 189 and the components within the second package 189 are provided in a sterile condition.

The kit optionally includes one or more dispensing tips 150C and dual piston 62C.

FIGS. 18 through 26 illustrate the use of the kit 20C to deliver a tissue adhesive and/or sealant. If the kit 20C is used to prepare and deliver a tissue adhesive and/or adhesive disclosed in U.S. Pat. No. 5,583,114, then the first and second components may be dispensed without being heated above room temperature. This removes any need to use the kit 20C in conjunction with heating and/or stirring instrumentation. This further simplifies the use of the kit 20C to prepare and deliver a tissue adhesive and/or sealant.

Preferably, the first and second containers 22C and 24C, the dispenser (e.g. 30C), the vial 174 and syringe and needle 28C are provided in sterile condition within first package 187 and the first package 187 is provided in a sterile fashion within a second package 189. In this fashion, the second package 189 may be opened by a healthcare worker outside a sterile area (e.g. a circulating nurse) and the first package 187 may be aseptically taken from the second package 189 and placed in the sterile area by a healthcare worker associated with the sterile area (e.g. a scrub nurse). The first and second packages 187 and 189 may include bags (e.g. pouches) or trays or combinations thereof. Trays offer an advantage in that they reduce the number of separate, individual waste products associated with the kit. If the packages 187 or 189 include a bag, they are preferably constructed from suitable materials capable of withstanding sterilization processes. For example, such materials include TYVEK and/or MYLAR.

Figure 18:
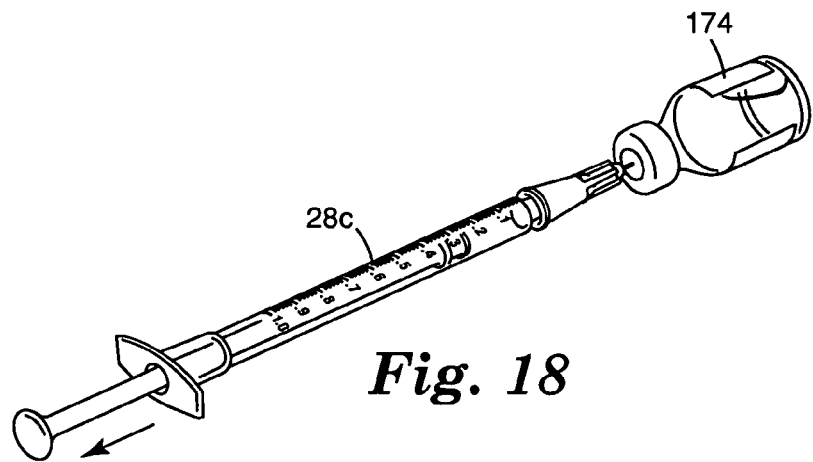
Figure 19:
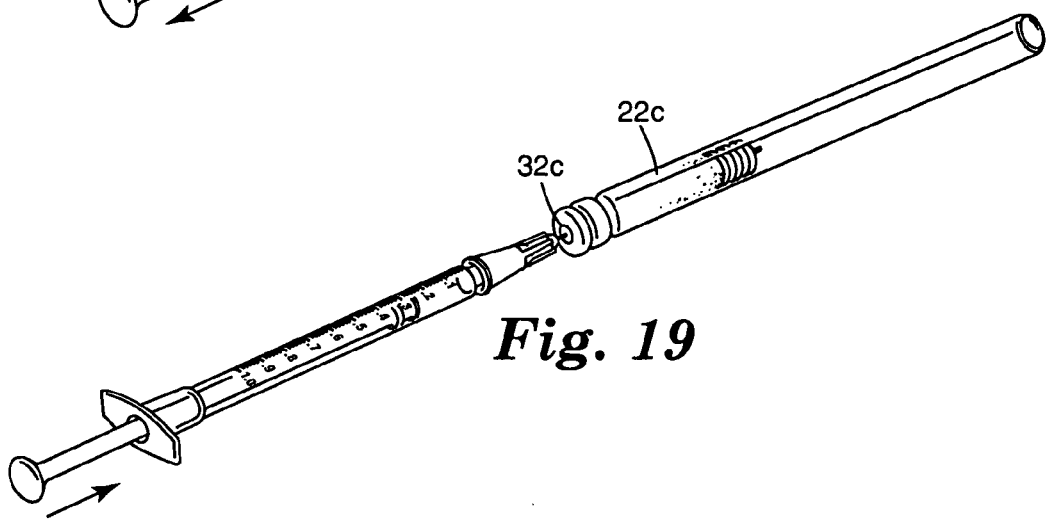

FIG. 18 illustrates the syringe 28C being used to remove the solvent from solvent container 174. The syringe 28C loaded with solvent may then be used to pierce the septum 32C of the container 22C and to inject the solvent for the first component into container 22C. Preferably, the steps shown in FIGS. 18 and 19 are conducted by a single healthcare worker (e.g. a scrub nurse). This may remove any need for one healthcare worker to coordinate with another healthcare worker in order to reconstitute any of the components of the tissue adhesive and/or sealant. Alternatively, the solvent may be stored within syringe 28C as the kit is provided (as described above), or the solvent may be stored within the storage bottle 174. This may have the advantage of making the task of sterilizing the total kit for surgical use more convenient.

Figure 20:
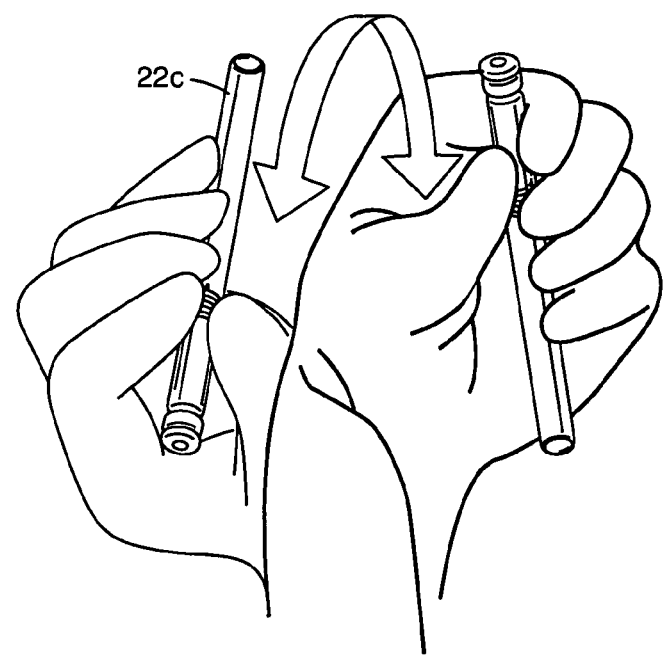
Figure 21:
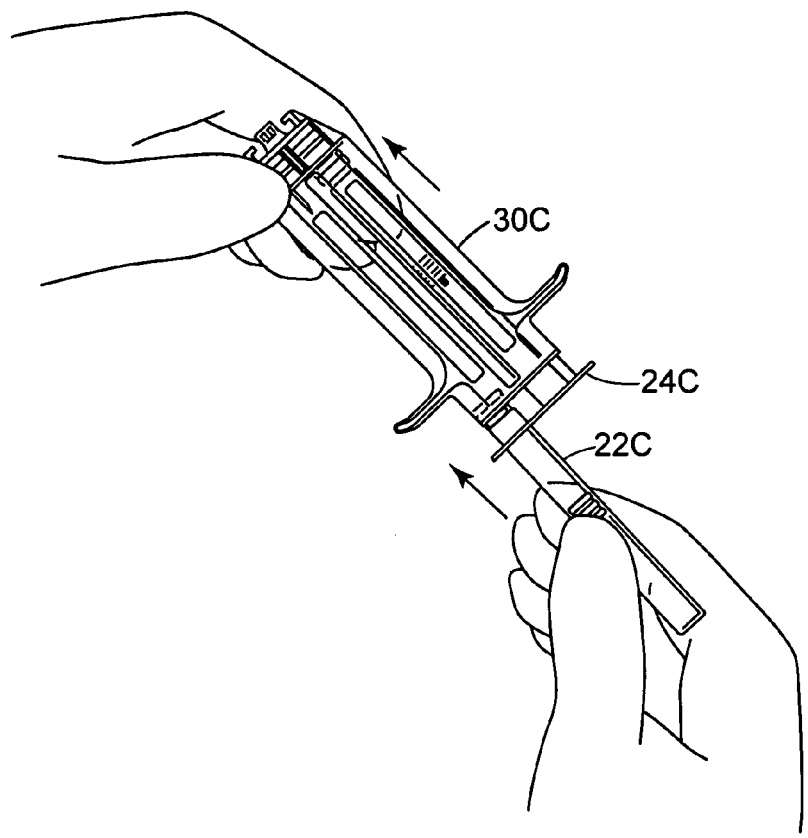

As shown in FIG. 20, the first container 22C is preferably agitated briefly to speed the process of dissolving the first component (e.g. a dry powder) in the solvent. Both containers 22C and 24C may then be inserted though holes in the retainer 129 and impaled on piercers 116B and 118B in the manner shown in FIG. 21. This can be readily conducted by a single healthcare worker without unduly exposing the healthcare worker to the piercers or requiring the healthcare worker to coordinate with another healthcare worker.

Figure 22:
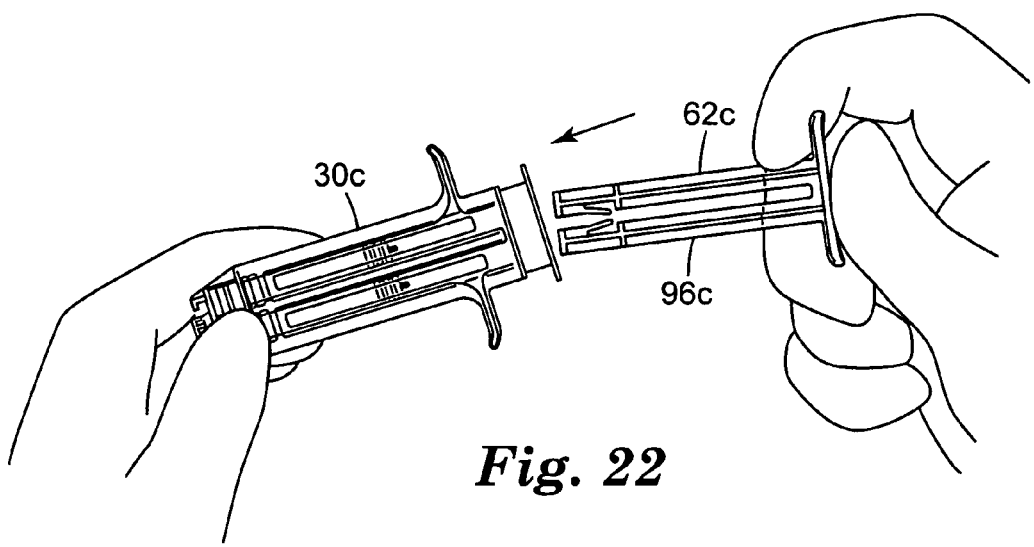

As shown in FIG. 22, dual plunger 62C is inserted into the retainer 129 and on into the distal ends of containers 22C and 24C, lightly touching movable plugs. Spring legs 176 on the dual plunger 62C may conveniently be placed on push rods 92C and 94C to provide a slight friction between the dual plunger 62C and the containers 22C and 24C so as to retain the dual plunger before use.

Figure 23:
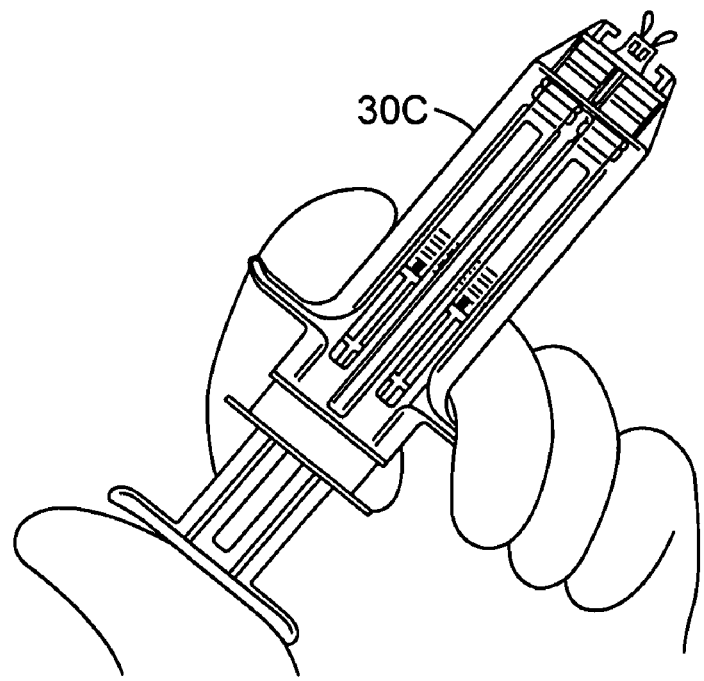
Figure 24:
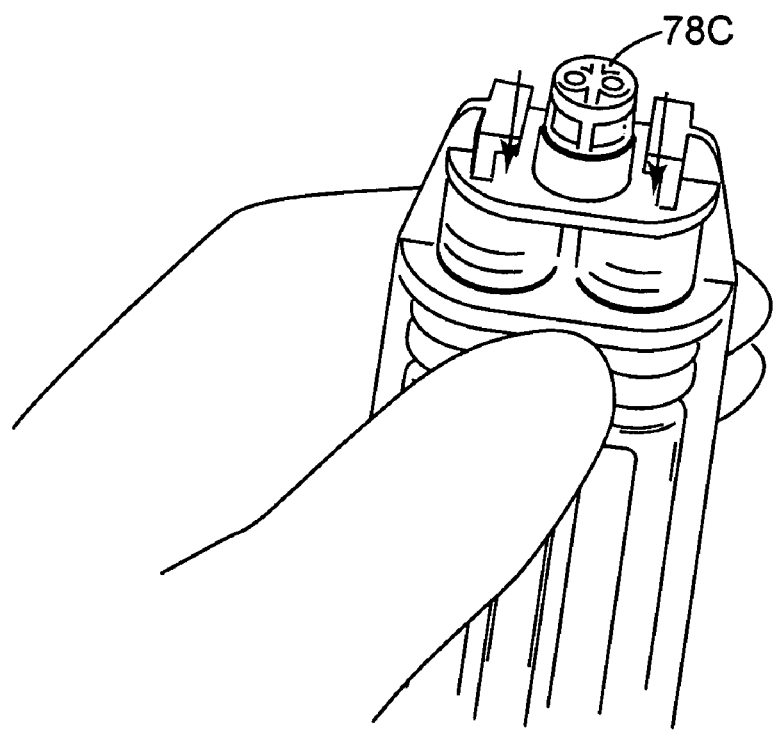

After the syringe 28C adds solution to the container 22C (see FIG. 19), some air remains in the container. As shown in FIG. 23, air is preferably expressed from the assembly. Preferably, after the syringe adds the solution to the powder, the movable member 38B (see FIG. 14 for the member 38B, not its position) is slightly axially offset relative to the movable member 50B so that the dual plunger 62B initially moves the movable member 38B to express the air without moving the movable member 50B. FIG. 14 illustrates the movable members 38B and 50B after the air has been expressed from the first container so that the movable members are substantially axially aligned. In FIG. 24, the distal end (nozzle) of the housing 30C is preferably wiped clean to provide a clean surface for receiving the dispensing tip 150C.

Figure 25:
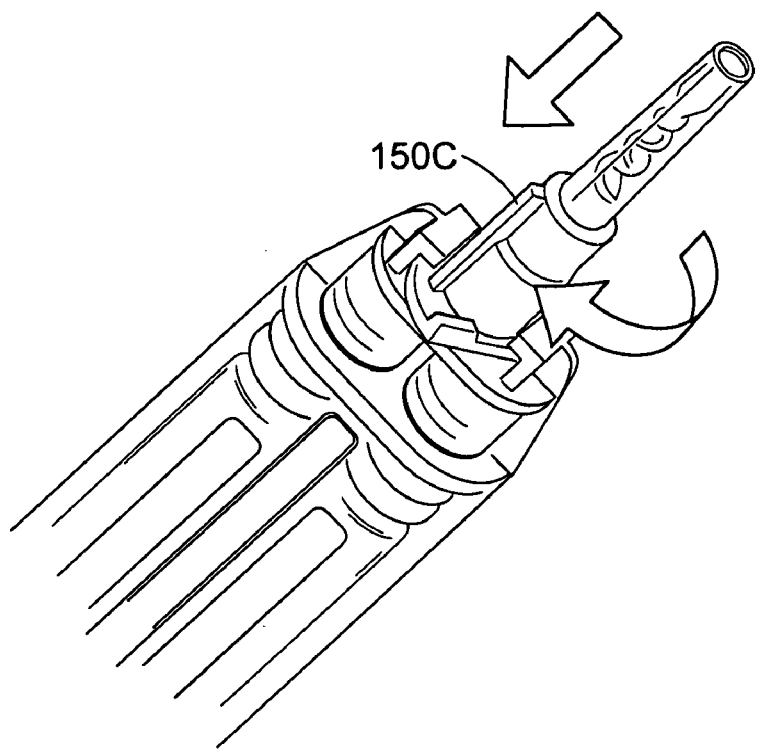

Optionally, but preferably, at least one dispensing tip 150C will be provided, and in some preferred embodiments a second tip will be provided. Placement of the dispensing tip 150C on the housing 30C is shown in FIG. 25. If only a portion of the contents of the containers 22C and 24C is dispensed, and then enough time passes that the mixture within the dispensing tip 150C crosslinks or cures sufficient to clog dispensing tip 150C, the second dispensing tip can be attached so that the remain contents of the containers 22C and 24C can be dispensed.

Figure 26:
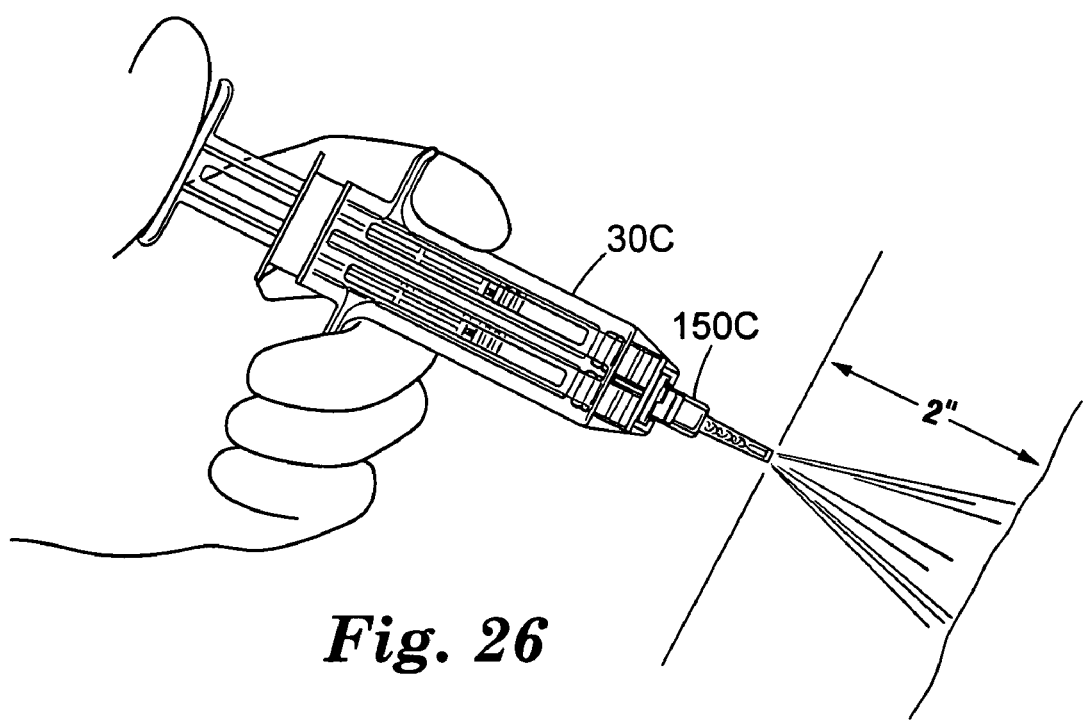

The tissue adhesive and or sealant may then be dispensed or applied as shown in FIG. 26. When the tissue sealant is a tissue sealant constructed according to one embodiment of the teachings of U.S. Pat. No. 5,583,114, "ADHESIVE SEALANT COMPOSITION," then the sealant is preferable dispensed about two inches from the tissue.

In some preferred embodiments, the elements depicted are conveniently packaged together, conveniently all on a single tray formed of e.g. polyethylene terephthalate, conveniently covered with a cover of e.g. TYVEK spun-bonded polyolefin heat sealed to the tray. If the several elements are most conveniently sterilized for surgical use using different sterilizing techniques, the kit may be provided in two packages, each holding the elements that are expeditiously sterilized together.

It should be noted that all of the steps shown in FIGS. 18–25 may be conducted by a single individual. The step of placing the solvent in the first container (FIG. 18) and the steps of installing the first and second containers in the dispenser (FIG. 22) and piercing the septums of the first and second containers (also FIG. 22) with the first and second piercers are especially convenient when conducted by a single healthcare worker as one healthcare worker need not coordinate activities with another healthcare worker.

Figure 16:
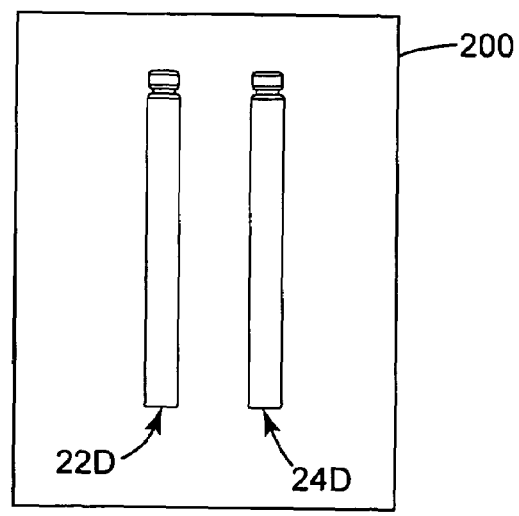
FIG. 16 is a top view of a minor subassembly of a kit according to one aspect of the present invention.
Figure 17:
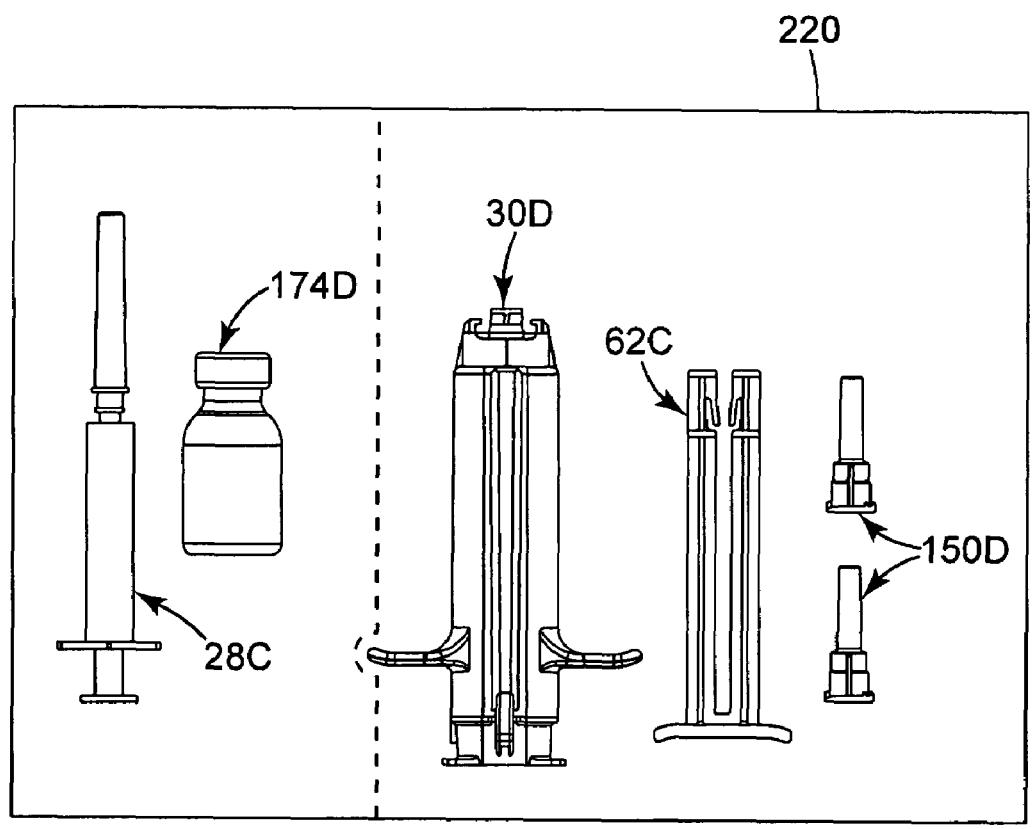
FIG. 17 is a top view of a major subassembly for use with the minor subassembly shown in FIG. 16 according to another aspect of the present invention.

FIGS. 16 and 17 illustrate another embodiment of kit according to the present invention. In FIG. 16, the first and second containers 22C and 24C may be provided in a separate minor subassembly kit 200. Alternatively, the entire preassembly P (See FIG. 11) may be provided in a minor subassembly kit.

FIG. 17 illustrates a major subassembly kit 220 that includes housing 30D, piston 62D, dispensing tips 150D, syringe and needle assembly 28D and solvent (e.g. water) bottle 174D.

The minor subassembly kit 200 may include those elements of the tissue adhesive and/or sealant that include a relatively short shelf life. For example, such labile elements may include a protein solution (e.g. albumin) and dry powder cross-linker component. In another aspect of the present invention, the minor subassembly kit 200 may include those elements of the tissue sealant and/or adhesive that require a different temperature range for storage than the components of the major subassembly kit 220. For example, the minor subassembly kit may include those items that require refrigeration until just prior to use.

In yet another aspect of the invention, the minor subassembly may include those elements of the tissue adhesive and or sealant dispenser that are packaged for a sterilization technique that is different than other portions of the tissue adhesive and or sealant dispenser. For example, the dry powder and liquid components of an adhesive tissue sealant may be sterilized within containers using a low dose e-beam technique (e.g. about 10–20 kGy) and then terminally sterilized using an ethylene oxide sterilization technique. However, the remaining portions of the dispenser need only be subjected to an ethylene oxide sterilization technique. In this embodiment, if the major subassembly includes all of the elements of the kit except containers 22C and 24C, then a majority of the elements of the kit can be sterilized without subjecting them to the effects of the e-beam sterilization technique.

Figure 27A:
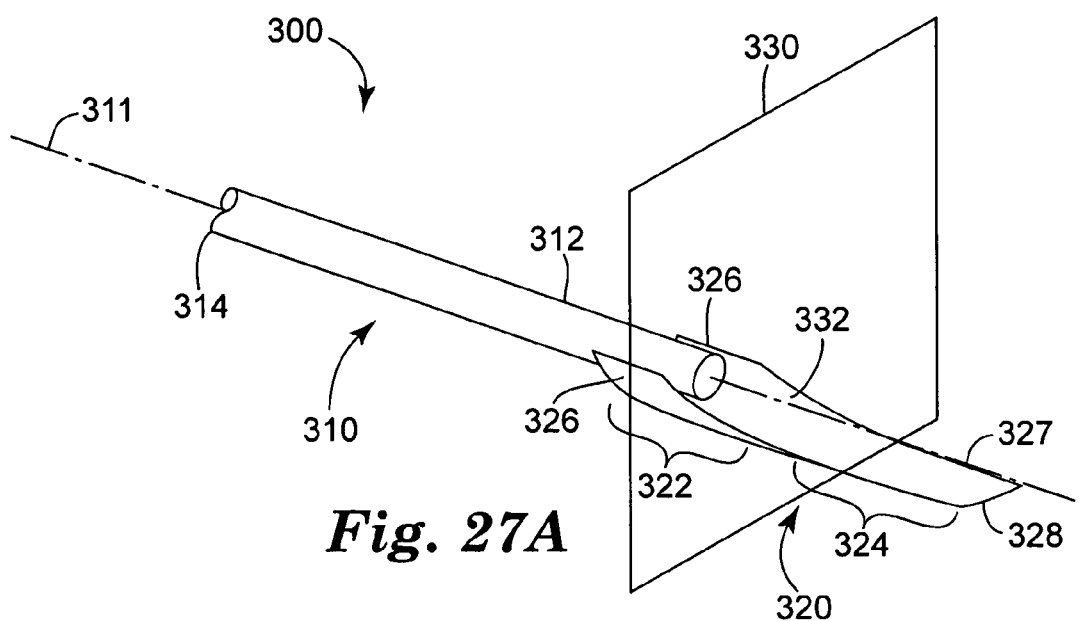
FIG. 27a is a perspective view of one applicator according to the present invention.

FIG. 27a illustrates another embodiment of the present invention including an applicator 300 to assist in dispensing and/or applying tissue sealant. The depicted applicator 300 includes a handle 310 and a blade 320. The handle 310 of the applicator 300 defines a longitudinal axis 311 with a first end 312. The blade 320 is attached to the first end 312 of the handle 310. A proximal portion 322 of the blade 320 may be attached by partially wrapping the blade 320 around the first end 312 of the handle 310. Attaching the blade 320 to the handle 310 may be accomplished by any suitable method known in the art, e.g., adhesives, heat sealing, clinching, riveting, tying, stapling, chemically adhering, mechanically fastening, welding (chemically or thermally), etc.

The handle 310 may be constructed of any suitable material known in the art, e.g., wood, plastic, metal, etc. Further, the handle 310 may be configured in a variety of shapes and lengths, including curved, ergonomically shaped, etc.

As illustrated in FIG. 27a, the blade 320 includes a proximal portion 322 proximate the first end 312 of the handle 310 and a terminal portion 324 distal from the first end 312 of the handle 310. The blade 320 may be partially wrapped around the first end 312 and attached by bonding or other suitable methods. This may allow for a stiffened proximal portion 322 and a flat terminal portion 324 of the blade 320 that is more flexible. The sides 326 of proximal portion 322 allow for accumulation of sealant to feed the terminal portion 324 as sealant is dispensed onto the tissue surface. This may allow more sealant material to be captured for spreading. The terminal portion 324 may be used, e.g., for painting the sealant onto delicate tissue as is further described below. In this embodiment, the proximal portion 322 of the blade 320 may be described as having a cross-section 332, taken in a plane 330 normal to a longitudinal axis 311 of the handle 310, that is U-shaped. Although the blade 320 depicted in FIG. 27a has a rectangular end, the blade 320 may alternatively be shaped for a variety of uses, including spoon-shaped, tapered, curved, etc. Medical personnel may also trim the blade 320 to fit a particular function or use.

The blade 320 may be constructed of any suitable material known in the art, e.g., polymeric materials, rubber, etc. The blade 320 may also be configured of single or multi-layered film sheets that can be customized to achieve desired flow and mixing characteristics. For example, using low surface energy materials for the blade may provide a surface that allows polymerized sealant on the tip to be wiped off so that the applicator 300 may be used again on the same patient. Further, the blade 320, which includes a first major surface 327 and a second major surface 328, may be manufactured such that the first major surface 327 and/or the second major surface 328 includes a structured surface, e.g., dams, grooves, microreplicated surfaces, etc. Further, the blade 320 may be rendered radiopaque, which can aid in locating blades or portions of blades that accidentally fall into a patient cavity. The blade 320 may have a tapered thickness, such that, e.g., the thickness of the blade 320 decreases along the edges of the blade 320 (which may improve blade flexibility at the edges).

Figure 27B:
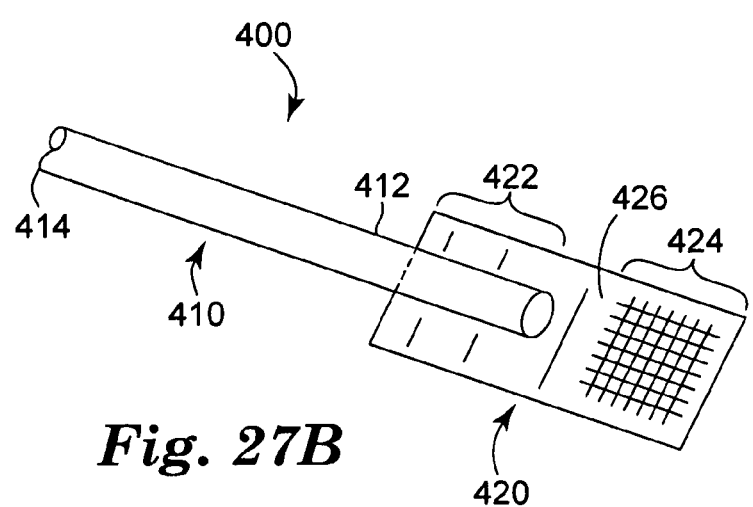
FIG. 27b is a perspective view of another applicator according to the present invention.

An alternative embodiment of an applicator 400 is depicted in FIG. 27b. As illustrated, applicator 400 is similar to the applicator 300 depicted in FIG. 27a. Applicator 400, however, includes a different blade 420, and the blade 420 is attached to the handle 410 in a slightly different manner. Blade 420 may be flat and attached to handle 410 without wrapping the proximal portion 422 of the blade 420 around the handle 410. In addition, the first major surface 426 of the terminal portion 424 is embossed.

Figure 28:
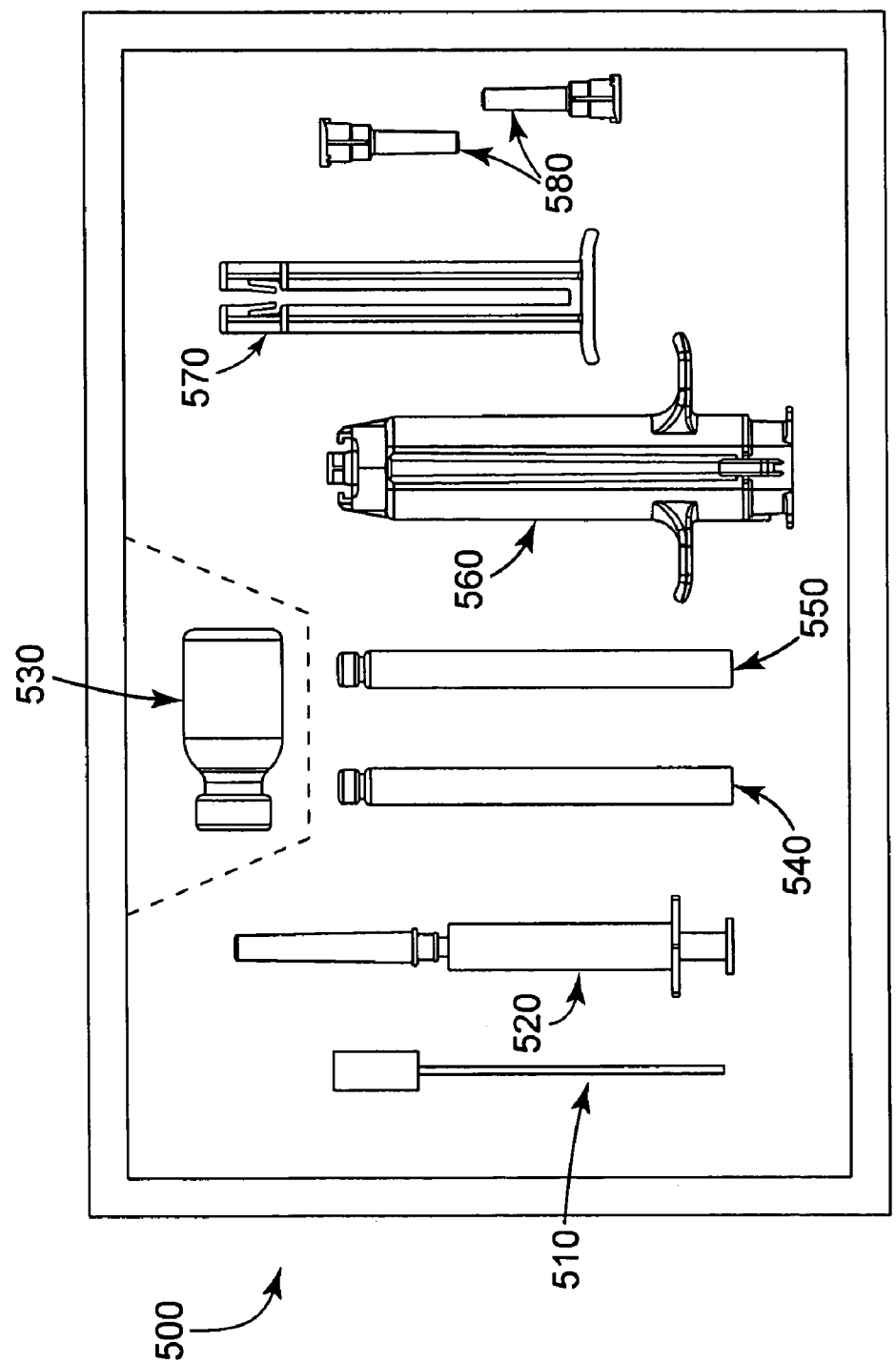
FIG. 28 is a plan view of another kit according to the present invention.

FIG. 28 illustrates another alternative embodiment of the present invention. A kit 500 similar to the kit depicted in FIG. 15 is illustrated. The kit 500 includes a syringe 520, a vial 530 containing a solvent, a first container 540 and a second container 550, a sterile housing 560 with plunger 570, and dispensing tips 580. In addition, the embodiment depicted in FIG. 28 also includes an applicator 510 as described above in connection with, e.g., FIGS. 27a and 27b.

Figure 29:
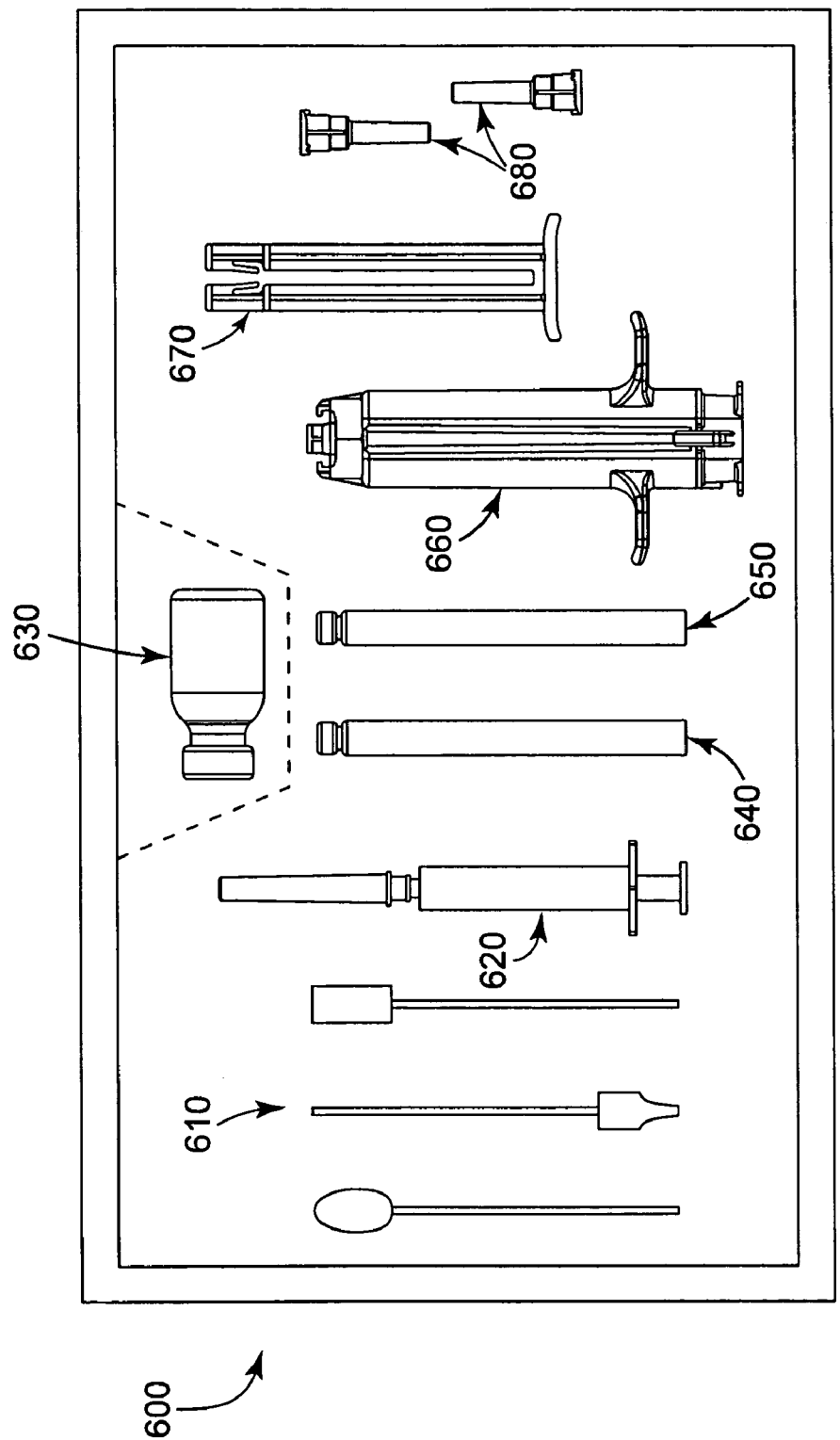
FIG. 29 is a plan view of another kit according to the present invention.

Although only one applicator 510 is depicted in connection with kit 500, the kits of the present invention may also include several different types of applicators to meet different situations that may be encountered when dispensing the adhesive tissue sealant of the present invention. For example, FIG. 29 illustrates a kit 600 that is similar to kit 500 of FIG. 28, except that kit 600 includes a plurality of applicators 610.

Figure 30:
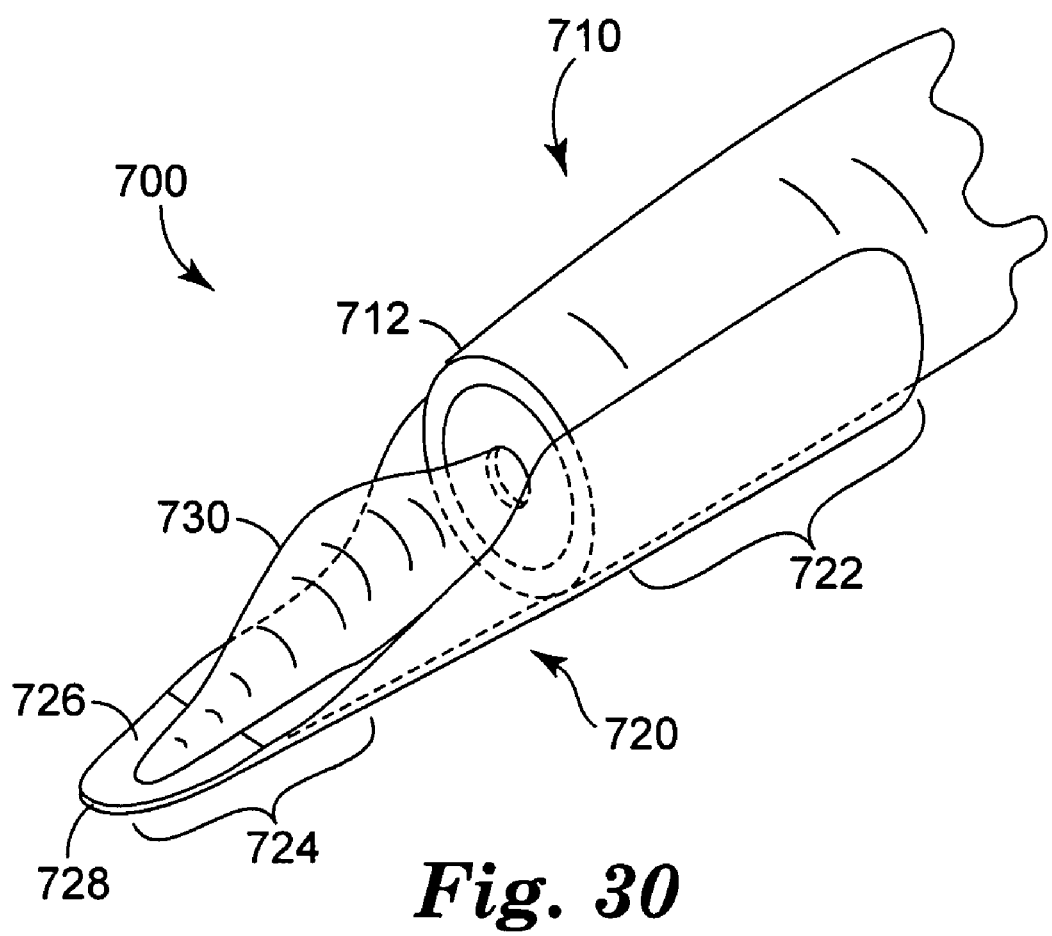
FIG. 30 is a perspective view of one dispensing tip with a blade according to the present invention.

In yet another embodiment of the present invention, a dispensing tip may be configured with a blade such that the adhesive tissue sealant may be brushed or spread while being dispensed. FIG. 30 illustrates this particular embodiment. As depicted in FIG. 30, dispensing tip assembly 700 includes a dispensing tip 710 and a blade 720. The blade 720 may include a proximal portion 722 proximate the dispensing tip 710 and a terminal portion 724 distal from the dispensing tip 710. The blade 720 is attached to a distal end 712 of the dispensing tip 710 by wrapping a proximal portion 722 of the blade 720 around the distal end 712 of the dispensing tip 710. This type of attachment allows for a stiffened proximal portion 722 and a substantially flat terminal portion 724 of the blade 720 wherein the flat terminal portion 724 is easily bendable. The sides of the stiffened proximal portion 722 allow for accumulation of sealant 730 to feed the terminal portion 724 as sealant 730 is dispensed onto the tissue surface. In this embodiment, the proximal portion 722 of the blade 720 may be described as having a cross-section, taken in a plane normal to a longitudinal axis of the dispensing tip 710, that is U-shaped.

The blade 720 may be constructed of any suitable material, e.g., polymeric materials, rubber, etc. Further, the blade 720, which includes a first major surface 726 and a second major surface 728, may be manufactured such that the first major surface 726 and/or the second major surface 728 includes a structured surface, e.g., dams, grooves, microreplicated surfaces, etc. Mixing and channeling features may also be incorporated into multi-layered film sheets to enhance flow characteristics, permit multiple sealant components, and to simplify and lower the cost of the dispensing tip assembly 700. The use of film offers a wide range of materials with various properties such as stiffness and hardness to achieve optimum painting effects. The shape of the blade 720 may be altered to allow varying thickness, widths, and end features such as square or rounded. Further, the blade 720 may be rendered radiopaque, which can aid in locating tips or portions of tips that accidentally fall into a patient cavity.

Although not depicted, it will be understood that the dispensing tip assembly 700 may include a substantially flat blade attached thereto (similar to the flat blade 420 of applicator 400).

Figure 31:
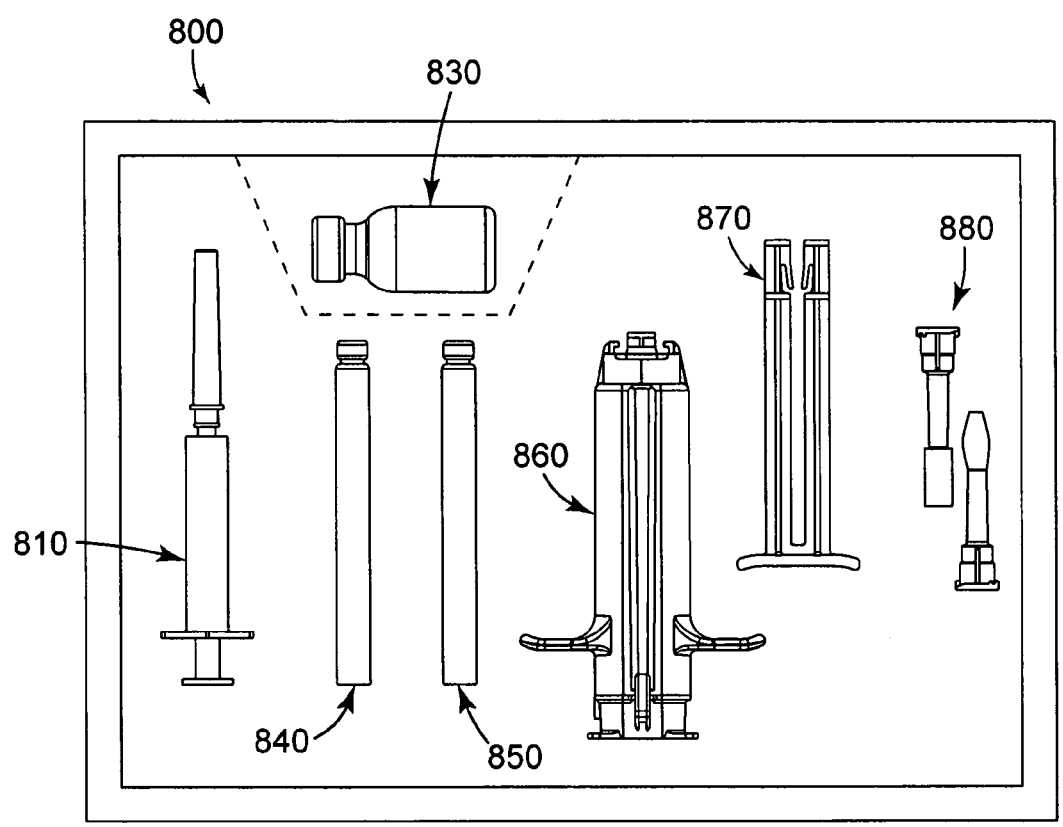
FIG. 31 is a plan view of another kit according to the present invention.

A kit as previously described may also be configured to include various dispensing tip assemblies. For example, FIG. 31 illustrates a kit 800 that includes components similar to those depicted in FIG. 15. Further, kit 800 includes a plurality of dispensing tip assemblies 880. The plurality of dispensing tip assemblies 880 may include a variety of dispensing tips and blades that are suited for multiple purposes. Although depicted as having two dispensing tip assemblies, the kits of the present invention may include none, one, or more dispensing tip assemblies.

Figure 32:
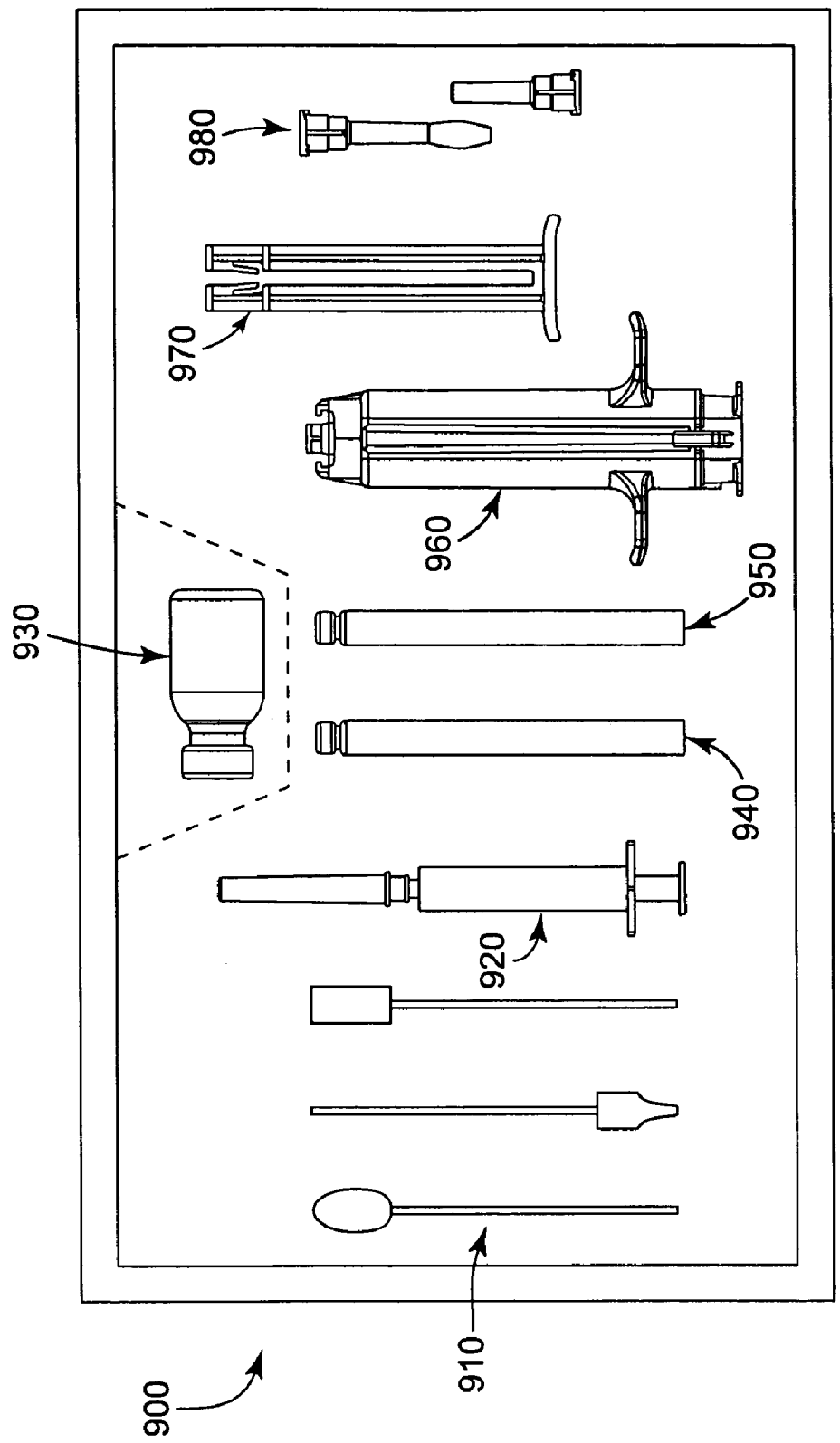
FIG. 32 is a plan view of another kit according to the present invention.

In addition, kits of the present invention may be configured to include not only dispensing tip assemblies, but applicators as well. As seen in FIG. 32, a dispensing kit 900 includes similar components as those illustrated in FIG. 31. Further, kit 900 may include a plurality of applicators 910.

Figure 33A:
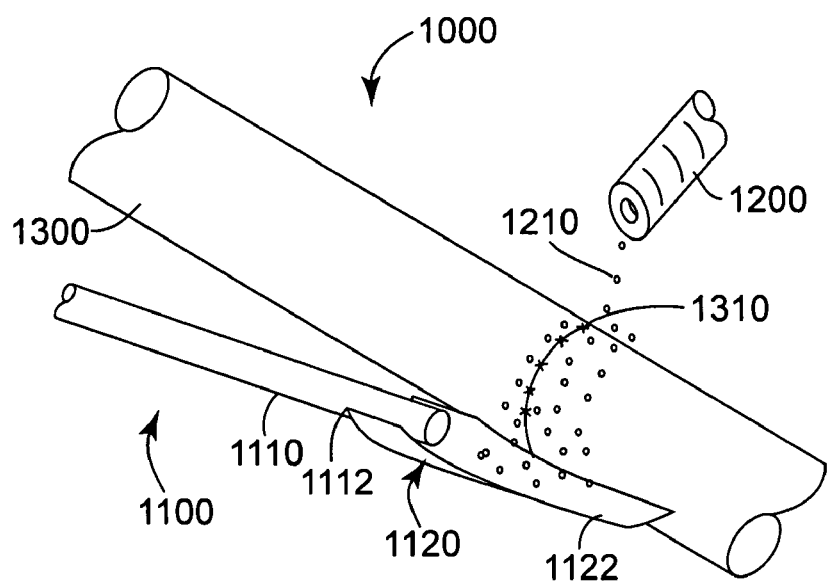
FIG. 33a illustrates use of an applicator according to the present invention to prepare a multiple component tissue sealant and/or adhesive.
Figure 33B:
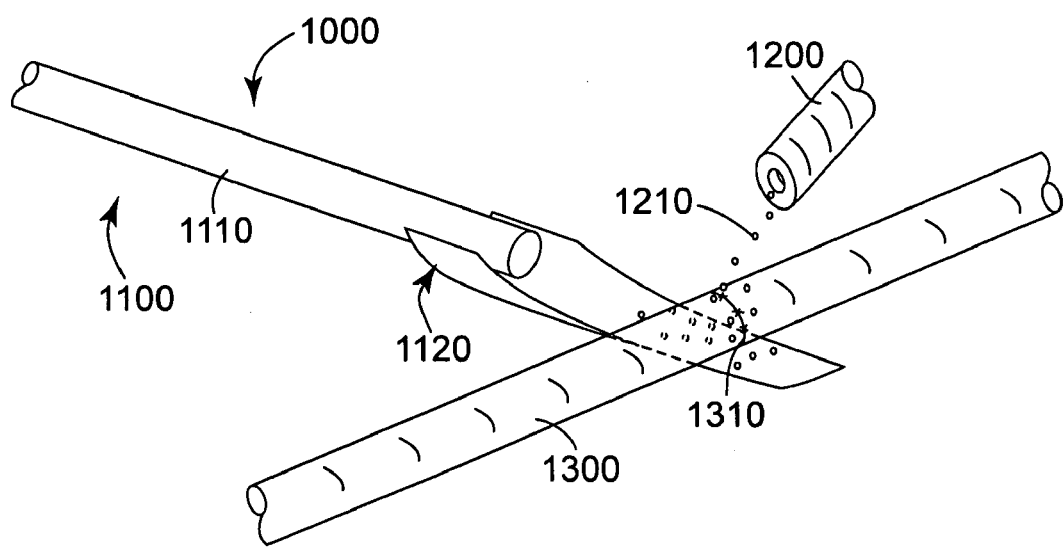
FIG. 33b illustrates use of an applicator according to the present invention to prepare a multiple component tissue sealant and/or adhesive.

FIGS. 33a and 33b illustrate another method of using the kit 600 of the present invention to deliver a tissue adhesive and/or sealant. In addition to the steps described above, the method further includes dispensing the tissue sealant 1210 from the dispensing tip 1200 onto the blade 1120 of the applicator 1100. The applicator 1100 is then manipulated independently of the housing (not shown) while dispensing the tissue sealant 1210. In other words, use of the applicator 1100 involves a two-handed technique whereby the applicator 1100 is used in one hand to catch and spread the sealant 1210 while the other hand is used to deliver the sealant 1210 to the site. This independent manipulation allows the user to dispense tissue sealant 1210 onto the blade 1120 and then apply the tissue sealant 1210 to the tissue surface 1310 of tissue 1300. Alternatively, the user may dispense tissue sealant 1210 first, followed by manipulation of the applicator 1100 after the tissue sealant 1210 has been dispensed onto the tissue surface 1310.

Tissue sealant 1210 may then be spread with the blade 1120. By placing the terminal end 1122 under a tissue surface or a vessel 1300, the applicator 1110 may be used to catch sealant 1210 that tends to run off of the tissue surface 1310. The use of the applicator 1100 may also help in applying tissue sealant 1210 to the underside of the tissue surface 1310, which can be difficult to access.

Additionally, the applicator 1100 allows application of sealant 1210 on the vertical or angled sides of organs and vessels by catching the sealant 1210 as it is dripped or sprayed onto the tissue surface 1310 of tissue 1300, as is illustrated in FIG. 33b. Normally, much of the tissue sealant 1210 could run off of the tissue 1300, but the applicator 1100 allows it to be spread back onto the tissue 1300 in a painting or troweling fashion to achieve a desired thickness over the area desired.

In yet another embodiment of the method of the present invention, a dispensing tip similar to dispensing tip 700 depicted in FIG. 30 may be used to spread tissue sealant 730 with the blade 720 by first dispensing tissue sealant 730 onto the blade 720 that is attached to the dispensing tip 710. The blade 720 is then manipulated such that tissue sealant 730 may be spread with the blade 720. Alternatively, the user may simultaneously dispense tissue sealant 730 onto the blade 720 while spreading the tissue sealant 730 with the blade 720.

Other embodiments of the invention are within the scope of the following claims. For example, in some aspects of the invention, materials other than an adhesive tissue sealant may be dispensed, or the solvent for dissolving the dry powder could be nonaqueous. More than two barrels and carpules (e.g., three) could be fitted to a syringe body and manifold. Individual pistons could be used instead of the dual piston. A kit may be sterilized as a whole (e.g. using e-beam or gamma sterilization techniques). Alternatively, individual components may be sterilized, the kit assembled, and then a terminal sterilization of the entire kit could occur.

All references and publications cited herein are expressly incorporated herein by reference in their entirety into this disclosure. Illustrative embodiments of this invention are discussed and reference has been made to possible variations within the scope of this invention. These and other variations and modifications in the invention will be apparent to those skilled in the art without departing from the scope of this invention, and it should be understood that this invention is not limited to the illustrative embodiments set forth herein. Accordingly, the invention is to be limited only by the claims provided below.

What is claimed is:

1. A kit comprising:
    a tissue sealant and/or adhesive having first and second component;
    a first container comprising a septum, wherein at least a portion of the first component is contained within the first container;
    a second container comprising a septum, wherein at least a portion of the second component is contained within the second container;
    a sterile housing comprising first and second piercers located in protected positions and a portion that is sized and shaped to receive the first and second containers;
    a dispensing tip comprising a longitudinal axis, wherein the dispensing tip is attachable to the housing; and
    a flexible blade attached to a distal end of the dispensing tip constructed to facilitate the application of a desired thickness of tissue sealant or adhesive dispensed from the dispensing tip.

2. The kit according to claim 1, wherein the blade comprises a proximal portion proximate the dispensing tip and a terminal portion distal from the dispensing tip, and further wherein the terminal portion of the blade is substantially flat.

3. The kit according to claim 1, wherein a cross-section of the proximal portion of the blade taken in a plane normal to the longitudinal axis of the dispensing tip comprises a U-shaped cross-section.

4. The kit according to claim 1, wherein the kit further comprises a plurality of dispensing tips.

5. The kit according to claim 4, wherein at least two dispensing tips of the plurality of dispensing tips comprise blades comprising different shapes.

6. The kit according to claim 1, wherein a cross-section of the blade taken in a plane normal to the longitudinal axis of the dispensing tip comprises a U-shaped cross-section.

7. The kit according to claim 1, wherein a cross-section of the blade taken proximate the dispensing tip in a plane normal to the longitudinal axis of the handle comprises a U-shaped cross-section.

8. The kit according to claim 1, wherein the blade comprises a spoon shape.

9. The kit according to claim 1, wherein the blade comprises first and second major surfaces, and further wherein the first major surface comprises a structured surface.

10. The kit according to claim 1, wherein the blade is embossed.

* * * * *

UNITED STATES PATENT AND TRADEMARK OFFICE
CERTIFICATE OF CORRECTION

PATENT NO. : 7,037,289 B2
APPLICATION NO. : 09/953037
DATED : May 2, 2006
INVENTOR(S) : Larry H. Dodge It is certified that error appears in the above-identified patent and that said Letters Patent is hereby corrected as shown below:

Column 18
In Claim 3, delete "claim 1," and insert in place thereof -- claim 2 -- .

Signed and Sealed this

Nineteenth Day of December, 2006

JON W. DUDAS
*Director of the United States Patent and Trademark Office*